United States Patent
Kiani et al.

(10) Patent No.: US 11,773,407 B2
(45) Date of Patent: Oct. 3, 2023

(54) CRISPR LOGIC CIRCUITS FOR SAFER AND CONTROLLABLE GENE THERAPIES

(71) Applicant: Arizona Board of Regents on behalf of Arizona State University, Scottsdale, AZ (US)

(72) Inventors: Samira Kiani, Scottsdale, AZ (US); Mo Reza Ebrahimkhani, Scottsdale, AZ (US); Swechchha Pradhan, Tempe, AZ (US); Farzaneh Moghadam, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/626,021

(22) PCT Filed: Jun. 26, 2018

(86) PCT No.: PCT/US2018/039583
§ 371 (c)(1),
(2) Date: Dec. 23, 2019

(87) PCT Pub. No.: WO2019/005856
PCT Pub. Date: Jan. 3, 2019

(65) Prior Publication Data
US 2021/0155954 A1 May 27, 2021

Related U.S. Application Data

(60) Provisional application No. 62/552,321, filed on Aug. 30, 2017, provisional application No. 62/524,956, filed on Jun. 26, 2017.

(51) Int. Cl.
*C12N 15/86* (2006.01)
*C12N 9/22* (2006.01)
*C12N 15/113* (2010.01)

(52) U.S. Cl.
CPC ............ *C12N 15/86* (2013.01); *C12N 9/22* (2013.01); *C12N 15/113* (2013.01); *C12N 2310/20* (2017.05); *C12N 2750/14143* (2013.01)

(58) Field of Classification Search
None
See application file for complete search history.

(56) References Cited

U.S. PATENT DOCUMENTS

| | | | | |
|---|---|---|---|---|
| 2008/0081780 A1* | 4/2008 | Matzuk | ............... | A61P 9/10 536/23.2 |
| 2016/0208288 A1* | 7/2016 | Liu | ............... | C12N 15/01 |
| 2016/0340661 A1* | 11/2016 | Cong | ............... | C12N 15/907 |
| 2020/0123567 A1 | 4/2020 | Kiani | | |
| 2020/0377871 A1 | 12/2020 | Ewaisha et al. | | |
| 2020/0377884 A1 | 12/2020 | Kiani | | |
| 2021/0154326 A1* | 5/2021 | Kiani | ............... | C12N 9/22 |

FOREIGN PATENT DOCUMENTS

| | | | |
|---|---|---|---|
| WO | 1998010088 A1 | 3/1998 | |
| WO | 2015089427 A1 | 6/2015 | |
| WO | 2017040786 A1 | 3/2017 | |
| WO | WO-2017040786 A1 * | 3/2017 | ............ C12N 15/87 |
| WO | 2020097344 A1 | 5/2020 | |
| WO | 2021030433 A1 | 2/2021 | |

OTHER PUBLICATIONS

Bhupinder et al. Molecular Reproduction and Development 59: pp. 25-32 (Year: 2001).*
Kiani et al. Nature Methods 12, pp. 1051-1055 (Year: 2015).*
Kiani et al. Nat Methods 12(11):supplemental information, pp. 1-34 (Year: 2015).*
Ventura A, et al. Cre-lox-regulated conditional RNA interference from transgenes. Proc Natl Acad Sci U S A. 2004;101(28):10380-5.
Veron, P. et al., "Major Subsets of Human Dendritic Cells Are Efficiently Transduced by Self-Complementary Adeno-Associated Virus Vectors 1 and 2", Journal of Virology, May 2007, vol. 81, No. 10, pp. 5385-5394 DOI:10.1128/JVI.02516-06.
Wang, Y., et al. "Ligand-inducible and liver-specific target gene expression in transgenic mice." Nature biotechnology 15.3 (1997): 239-243.
Wang, Y., et al. "Positive and negative regulation of gene expression in eukaryotic cells with an inducible transcriptional regulator." Gene therapy 4.5 (1997): 432-441.
Warner, N. et al., "MyD88: A Critical Adaptor Protein in Innate Immunity Signal Transduction", The Journal of Immunology, Jan. 2013 (available online Dec. 2012), vol. 190, No. 1, pp. 3-4 DOI:10.4049/immunol.1203103.
Wu Y, et al. Correction of a genetic disease in mouse via use of CRISPR-Cas9. Cell Stem Cell. 2013;13(6):659-62.
Xia H, et al. siRNA-mediated gene silencing in vitro and in vivo. Nat Biotechnol. 2002;20(10):1006-10.
Xie F, et al. Seamless gene correction of beta-thalassemia mutations in patient-specific iPSCs using CRISPR/Cas9 and piggyBac. Genome Res. 2014;24(9):1526-33.
Xie K, et al. Boosting CRISPR/Cas9 multiplex editing capability with the endogenous tRNA-processing system. Proc Natl Acad Sci U S A. 2015;112(11):3570-5.
Xing Z, et al. Adenoviral vector-mediated interleukin-10 expression in vivo: intramuscular gene transfer inhibits cytokine responses in endotoxemia. Gene Ther. 1997;4(2):140-9.

(Continued)

*Primary Examiner* — Brian Whiteman
(74) *Attorney, Agent, or Firm* — Quarles & Brady LLP

(57) ABSTRACT

Aspects of the disclosure relate to synthetic regulatory systems composed of a multifunctional Cas nuclease, at least two guide RNAs (gRNAs) configured to target distinct nucleotide sequences, and a multilayered regulatory control element comprising ribozyme-based safety switches providing spatial and temporal control over the synthetic circuit in vivo.

14 Claims, 24 Drawing Sheets

(56) References Cited

OTHER PUBLICATIONS

Xue Hy, et al. In vivo gene therapy potentials of CRISPR-Cas9. Gene Ther. 2016;23(7):557-9.
Yang Y, et al. A dual AAV system enables the Cas9-mediated correction of a metabolic liver disease in newborn mice. Nat Biotechnol. 2016;34(3):334-8.
Yao, Z. et al., "Blood-Borne Lipopolysaccharide Is Rapidly Eliminated by Liver Sinusoidal Endothelial Cells via High-Density Lipoprotein", The Journal of Immunology, Sep. 2016, vol. 197, No. 6, pp. 2390-2399 DOI:10.4049/immunol.1600702.
Yeo, N. et al., "An enhanced CRISPR repressor for targeted mammalian gene regulation", Nature Methods, Aug. 2018, vol. 15, pp. 611-616 DOI:10.1038/s41592-018-0048-5.
Yin H, et al. Genome editing with Cas9 in adult mice corrects a disease mutation and phenotype. Nat Biotechnol. 2014;32(6):551-3.
Yonaha M, et al. Cell cycle-dependent regulation of RNA polymerase II basal transcription activity. Nucleic acids research. 1995;23(20):4050-4.
Yu, G. et al., "clusterProfiler: an R Package for Comparing Biological Themes Among Gene Clusters", OMICS: A Journal of Integrative Biology, May 2012, vol. 16, No. 5, pp. 284-287 DOI:10.1089/omi.2011.0118.
Yu, M. et al., "MyD88-dependent interplay between myeloid and endothelial cells in the initiation and progression of obesity-associated inflammatory diseases", Journal of Experimental Medicine, Apr. 2014, vol. 211, No. 5, pp. 887-907 DOI:10.1084/jem.20131314.
Zalatan JG, et al. Engineering complex synthetic transcriptional programs with CRISPR RNA scaffolds. Cell. 2015;160(1-2):339-50.
Zhang, H. et al., "Sepsis Induces Hematopoietic Stem Cell Exhaustion and Myelosuppression through Distinct Contributions of TRIF and MYD88", Stem Cell Reports, Jun. 2016, vol. 6, No. 6, pp. 940-956 DOI:10.1016/j.stemcr.2016.05.002.
Zheng, Y. et al., "CRISPR interference-based specific and efficient gene inactivation in the brain", Nature Neuroscience, Feb. 2018, vol. 21, pp. 447-454 DOI:10.1038/s41593-018-0077-5.
Zhou, H. et al., "In vivo simultaneous transcriptional activation of multiple genes in the brain using CRISPR-dCas9-activator transgenic mice", Nature Neuroscience, Jan. 2018, vol. 21, pp. 440-446 DOI: 10.1038/s41593-017-0060-6.
Zhu, J. et al., "The TLR9-MyD88 pathway is critical for adaptive immune responses to adeno-associated virus gene therapy vectors in mice", The Journal of Clinical Investigation, Jul. 2009, vol. 119, No. 8, pp. 2388-2398 DOI:10.1172/JCI37607.
U.S. Appl. No. 16/626,013, filed Dec. 23, 2019, Kiani et al. titled "CRISPR-Based Synthetic Gene Circuits as Next Generation Gene Therapy of Inner Ear".
U.S. Appl. No. 16/973,421, filed Dec. 8, 2020, Ebrahimkhani et al. titled "Next Generation Designer Liver Organoids and Their Methods of Preparation and Use".
Alexander S, et al. Protection from endotoxemia by adenoviral-mediated gene transfer of human bactericidal/permeability-increasing protein. Blood. 2004;103(1):93-9.
Alton EW, et al. Repeated nebulisation of non-viral CFTR gene therapy in patients with cystic fibrosis: a randomised, double-blind, placebo-controlled, phase 2b trial. Lancet Respir Med. 2015;3(9):684-91.
Anders, S. et al., "Differential expression analysis for sequence count data", Genome Biology, Oct. 2010, vol. 11, No. R106, pp. 1-12.
Beal J. Signal-to-Noise Ratio Measures Efficacy of Biological Computing Devices and Circuits. Front Bioeng Biotechnol. 2015;3:93.
Blazeck J, et al. Promoter engineering: recent advances in controlling transcription at the most fundamental level. Biotechnol J. 2013;8(1):46-58.
Bregman DB, et al. Cell cycle regulation and RNA polymerase II. Frontiers in bioscience : a journal and virtual library. 2000;5:D244-57.
Chavez A, et al. Comparison of Cas9 activators in multiple species. Nat Methods. 2016;13(7):563-7.
Chavez A, et al. Highly efficient Cas9-mediated transcriptional programming. Nat Methods. 2015;12(4):326-8.
Chen Y, et al. A Self-restricted CRISPR System to Reduce Off-target Effects. Molecular therapy : the journal of the American Society of Gene Therapy. 2016;24(9):1508-10.
Chew WL, et al. A multifunctional AAV-CRISPR-Cas9 and its host response. Nat Methods. 2016;13(10):868-74.
Cho, S-Y. et al., "Biomarkers of Sepsis", Infection & Chemotherapy, Mar. 2014, vol. 46, No. 1, pp. 1-12 DOI:10.3947/ic.2014.46.1.1.
Cicalese MP, et al. Clinical applications of gene therapy for primary immunodeficiencies. Hum Gene Ther. 2015;26(4):210-9.
Cong L, et al. Comprehensive interrogation of natural TALE DNA-binding modules and transcriptional repressor domains. Nat Commun. 2012;3:968.
Cook-Mills, J. et al., "Vascular Cell Adhesion Molecule-1 Expression and Signaling During Disease: Regulation by Reactive Oxygen Species and Antioxidants", Antioxidants & Redox Signaling, Aug. 2011 (available online Nov. 2010), vol. 15, No. 6, pp. 1607-1638 DOI:10.1089/ars.2010.3522.
Couzin-Frankel J. Breakthrough of the year 2013. Cancer immunotherapy. Science. 2013;342(6165):1432-3.
Cuccato G, et al. Systems and Synthetic biology: tackling genetic networks and complex diseases. Heredity (Edinb). 2009;102(6):527-32.
Dahlman JE, et al. Orthogonal gene knockout and activation with a catalytically active Cas9 nuclease. Nat Biotechnol. 2015;33(11):1159-61.
Dandekar, A. et al., "Toll-like Receptor (TLR) Signaling Interacts with CREBH to Modulate High-density Lipoprotein (HDL) in Response to Bacterial Endotoxin", Journal of Biological Chemistry, Oct. 2016, vol. 291, No. 44, pp. 23149-23158 DOI:10.1074/jbc.M116.755728.
Davidsohn N, et al. Accurate predictions of genetic circuit behavior from part characterization and modular composition. ACS Synth Biol. 2015;4(6):673-81.
De Solis CA, et al. The Development of a Viral Mediated CRISPR/Cas9 System with Doxycycline Dependent gRNA Expression for Inducible In vitro and In vivo Genome Editing. Frontiers in molecular neuroscience. 2016;9:70.
Denham W, et al. Transient human gene therapy: a novel cytokine regulatory strategy for experimental pancreatitis. Annals of surgery. 1998;227(6):812-20.
Ding Q, et al. Permanent alteration of PCSK9 with in vivo CRISPR-Cas9 genome editing. Circulation research. 2014;115(5):488-92.
Donsante A, et al. AAV vector integration sites in mouse hepatocellular carcinoma. Science. 2007;317(5837):477.
Ebrahimkhani MR, et al. Aag-initiated base excision repair promotes ischemia reperfusion injury in liver, brain, and kidney. Proc Natl Acad Sci U S A. 2014;111(45):E4878-86.
Ebrahimkhani MR, et al. Cross-presentation of antigen by diverse subsets of murine liver cells. Hepatology. 2011;54(4):1379-87.
Ebrahimkhani MR, et al. Naltrexone, an opioid receptor antagonist, attenuates liver fibrosis in bile duct ligated rats. Gut. 2006;55(11):1606-16.
Ebrahimkhani MR, et al. Stimulating healthy tissue regeneration by targeting the 5-HT(2)B receptor in chronic liver disease. Nat Med. 2011;17(12):1668-73.
Feng YF, et al. Lipopolysaccharide Promotes Choroidal Neovascularization by Up-Regulation of CXCR4 and CXCR7 Expression in Choroid Endothelial Cell. PLoS One. 2015;10(8):e0136175.
Ferry QR, et al. Rational design of inducible CRISPR guide RNAs for de novo assembly of transcriptional programs. Nat Commun. 2017;8:14633.
Filonov GS, et al. Broccoli: rapid selection of an RNA mimic of green fluorescent protein by fluorescence-based selection and directed evolution. Journal of the American Chemical Society. 2014;136(46):16299-308.
Gao Y, et al. Self-processing of ribozyme-flanked RNAs into guide RNAs in vitro and in vivo for CRISPR-mediated genome editing. Journal of integrative plant biology. 2014;56(4):343-9.

(56) References Cited

OTHER PUBLICATIONS

Gee AP. Manufacturing genetically modified T cells for clinical trials. Cancer Gene Ther. 2015;22(2):67-71.
Giering JC, et al. Expression of shRNA from a tissue-specific pol II promoter is an effective and safe RNAi therapeutic. Molecular therapy : the journal of the American Society of Gene Therapy. 2008;16(9):1630-6.
Ginn SL, et al. Gene therapy clinical trials worldwide to 2012—an update. J Gene Med. 2013;15(2):65-77.
Gossen, M., et al. "Tight control of gene expression in mammalian cells by tetracycline-responsive promoters." Proceedings of the National Academy of Sciences 89.12 (1992): 5547-5551.
Gossen, M., et al. "Transcriptional activation by tetracyclines in mammalian cells." Science 268.5218 (1995): 1766-1769.
Greenberg B, et al. Design of a phase 2b trial of intracoronary administration of AAV1/SERCA2a in patients with advanced heart failure: the CUPID 2 trial (calcium up-regulation by percutaneous administration of gene therapy in cardiac disease phase 2b). JACC Heart Fail. 2014;2(1):84-92.
Grimm D, et al. In vitro and in vivo gene therapy vector evolution via multispecies interbreeding and retargeting of adeno-associated viruses. Journal of virology. 2008;82(12):5887-911.
Hacein-Bey-Abina S, et al. Insertional oncogenesis in 4 patients after retrovirus-mediated gene therapy of SCID-X1. J Clin Invest. 2008;118(9):3132-42.
Haft, D. H., et al. "A guild of 45 CRISPR-associated (Cas) protein families and multiple CRISPR/Cas subtypes exist in prokaryotic genomes." PLoS computational biology 1.6 (2005).
Hale CR, et al. RNA-guided RNA cleavage by a CRISPR RNA-Cas protein complex. Cell. 2009;139(5):945-56.
Hamilton TA, et al. Regulation of macrophage gene expression by pro- and anti-inflammatory cytokines. Pathobiology : journal of immunopathology, molecular and cellular biology. 1999;67(5-6):241-4.
Harvey, D. M. "Inducible control of gene expression: prospects for gene therapy." Current opinion in chemical biology 2.4 (1998): 512-518.
Haurwitz RE, et al. Sequence- and structure-specific RNA processing by a CRISPR endonuclease. Science. 2010;329(5997):1355-8.
Herzog RW, et al. Two decades of clinical gene therapy—success is finally mounting. Discov Med. 2010;9(45):105-11.
Howe SJ, et al. Insertional mutagenesis combined with acquired somatic mutations causes leukemogenesis following gene therapy of SCID-X1 patients. J Clin Invest. 2008;118(9):3143-50.
Huang, X. et al., "Targeting the TLR9-MyD88 pathway in the regulation of adaptive immune responses", Expert Opinion on Therapeutic Targets, Jun. 2010, vol. 14, No. 8, pp. 787-796 DOI:10.1517/14728222.2010.501333.
International Searching Authority, International Search Report and Written Opinion for application PCT/US2018/039583, dated Nov. 29, 2018.
Janssens, S. et al., "A universal role for MyD88 in TLR/IL-1R-mediated signaling", Trends in Biochemical Sciences, Sep. 2002, vol. 27, No. 9, pp. 474-482 DOI:10.1016/S0968-0004(02)02145-X.
Chen, S. et al., "Efficient Transduction of Vascular Endothelial Cells with Recombinant Adeno-Associated Virus Serotype 1 and 5 Vectors", Human Gene Therapy, Mar. 2005, vol. 16, No. 2, pp. 235-247.
Jiang W, et al. RNA-guided editing of bacterial genomes using CRISPR-Cas systems. Nat Biotechnol. 2013;31(3):233-9.
Jinek M, et al. A programmable dual-RNA-guided DNA endonuclease in adaptive bacterial immunity. Science. 2012;337(6096):816-21.
Johnson LA, et al. Gene therapy with human and mouse T-cell receptors mediates cancer regression and targets normal tissues expressing cognate antigen. Blood. 2009;114(3):535-46.
Kiani S, et al. CRISPR transcriptional repression devices and layered circuits in mammalian cells. Nat Methods. 2014;11(7):723-6.
Knight SC, et al. Dynamics of CRISPR-Cas9 genome interrogation in living cells. Science. 2015;350(6262):823-6.
Kumar SR, et al. Clinical development of gene therapy: results and lessons from recent successes. Mol Ther Methods Clin Dev. 2016;3:16034.
Ledford H. Targeted gene editing enters clinic. Nature. 2011;471(7336):16.
Lee RJ, et al. VEGF gene delivery to myocardium: deleterious effects of unregulated expression. Circulation. 2000;102(8):898-901.
Lee, K. et al., "Isobavachalcone attenuates lipopolysaccharide-induced ICAM-1 expression in brain endothelial cells through blockade of toll-like receptor 4 signaling pathways", European Journal of Pharmacology, May 2015, vol. 754, pp. 11-18 DOI:10.1016/j.ejphar.2015.02.013.
Li L, et al. Challenges in CRISPR/CAS9 Delivery: Potential Roles of Nonviral Vectors. Hum Gene Ther. 2015;26(7):452-62.
Liao, H-K. et al., "In Vivo Target Gene Activation via CRISPR/Cas9-Mediated Trans-epigenetic Modulation", Cell, Dec. 2017, vol. 171, No. 7, pp. 1495-1507 DOI:10.1016/j.cell.2017.10.025.
Liao, H-K. et al., "Use of the CRISPR/Cas9 system as an intracellular defense against HIV-1 infection in human cells", Nature Communications, Mar. 2015, vol. 6, No. 6413, pp. 1-10 DOI:10.1038/ncomms7413.
Lienert F, et al. Synthetic biology in mammalian cells: next generation research tools and therapeutics. Nat Rev Mol Cell Biol. 2014;15(2):95-107.
Lin X, et al. Development of a tightly regulated U6 promoter for shRNA expression. FEBS letters. 2004;577(3):376-80.
Lin, X. et al., "Effect of TLR4/MyD88 Signaling Pathway on Expression of IL-1 and TNF- in Synovial Fibroblasts from Temporomandibular Joint Exposed to Lipopolysaccharide", Mediators of Inflammation, Feb. 2015, vol. 2015, article 329405, pp. 1-11 DOI:10.1155/2015/329405.
Liu Y, et al. Directing cellular information flow via CRISPR signal conductors. Nat Methods. 2016;13(11):938-44.
Losordo DW, et al. Gene therapy for myocardial angiogenesis: initial clinical results with direct myocardial injection of phVEGF165 as sole therapy for myocardial ischemia. Circulation. 1998;98(25):2800-4.
Lu, Y. et al., "Distinct immune responses to transgene products from rAAV1 and rAAV8 vectors", Proceedings of the National Academy of Sciences of the United States of America, Oct. 2009, vol. 106, No. 40, pp. 17158-17162 DOI:10.1073/pnas.0909520106.
Ma, X-Y. et al., "Early prevention of trauma-related infection/sepsis", Military Medical Research, Nov. 2016, vol. 3, No. 33, pp. 1-7 DOI:10.1186/s40779-016-0104-3.
Magari, S. R., et al. "Pharmacologic control of a humanized gene therapy system implanted into nude mice." The Journal of clinical investigation 100.11 (1997): 2865-2872.
Maji B, et al. Multidimensional chemical control of CRISPR-Cas9. Nature chemical biology. 2017;13(1):9-11.
Mali P, et al. RNA-guided human genome engineering via Cas9. Science. 2013;339(6121):823-6.
Marshall E. Gene therapy death prompts review of adenovirus vector. Science. 1999;286(5448):2244-5.
McCarthy Ho, et al. Bioreductive GDEPT using cytochrome P450 3A4 in combination with AQ4N. Cancer Gene Ther. 2003;10(1):40-8.
Mingozzi F, et al. Immune responses to AAV vectors: overcoming barriers to successful gene therapy. Blood. 2013;122(1):23-36.
Mohar I, et al. Isolation of Non-parenchymal Cells from the Mouse Liver. Methods Mol Biol. 2015;1325:3-17.
Moreno, A. et al., "In Situ Gene Therapy via AAV-CRISPR-Cas9-Mediated Targeted Gene Regulation", Molecular Therapy, Apr. 2018, vol. 26, No. 7, pp. 1818-1827 DOI:10.1016/j.ymthe.2018.04.017.
Morgan RA, et al. Cancer regression in patients after transfer of genetically engineered lymphocytes. Science. 2006;314(5796):126-9.
Muchamuel T, et al. IL-13 protects mice from lipopolysaccharide-induced lethal endotoxemia: correlation with down-modulation of TNF-alpha, IFN-gamma, and IL-12 production. J Immunol. 1997;158(6):2898-903.

(56) References Cited

OTHER PUBLICATIONS

Nault JC, et al. Recurrent AAV2-related insertional mutagenesis in human hepatocellular carcinomas. Nature genetics. 2015;47(10):1187-93.

No, D., et al. "Ecdysone-inducible gene expression in mammalian cells and transgenic mice." Proceedings of the National Academy of Sciences 93.8 (1996): 3346-3351.

Pakala SB, et al. MTA1 coregulator regulates LPS response via MyD88-dependent signaling. The Journal of biological chemistry. 2010;285(43):32787-92.

Park, G-S. et al., "LPS Up-Regulates ICAM-1 Expression in Breast Cancer Cells by Stimulating a MyD88-BLT2-ERK-Linked Cascade, Which Promotes Adhesion to Monocytes", Molecules and Cells, Aug. 2015, vol. 38, No. 9, pp. 821-828 DOI:10.14348/molcells.2015.0174.

Pineda M, et al. Engineered CRISPR Systems for Next Generation Gene Therapies. ACS Synth Biol. 2017. Epub May 31, 2017.

Raper SE, et al. Fatal systemic inflammatory response syndrome in a ornithine transcarbamylase deficient patient following adenoviral gene transfer. Mol Genet Metab. 2003;80(1-2):148-58.

Reardon S. Leukaemia success heralds wave of gene-editing therapies. Nature. 2015;527(7577):146-7.

Rosadini CV, et al. Early innate immune responses to bacterial LPS. Current opinion in immunology. 2017;44:14-9. Epub Nov. 15, 2016.

Russell DW. AAV vectors, insertional mutagenesis, and cancer. Molecular therapy : the journal of the American Society of Gene Therapy. 2007;15(10):1740-3.

Salcedo R, et al. Vascular endothelial growth factor and basic fibroblast growth factor induce expression of CXCR4 on human endothelial cells: In vivo neovascularization induced by stromal-derived factor-1alpha. Am J Pathol. 1999;154(4):1125-35.

Savic N, et al. Advances in therapeutic CRISPR/Cas9 genome editing. Transl Res. 2016;168:15-21.

Schnare, M. et al., "Toll-like receptors control activation of adaptive immune responses", Nature Immunology, Oct. 2001, vol. 2, pp. 947-950 DOI:10.1038/ni712.

Schwank G, et al. Functional repair of CFTR by CRISPR/Cas9 in intestinal stem cell organoids of cystic fibrosis patients. Cell Stem Cell. 2013;13(6):653-8.

Serrano L. Synthetic biology: promises and challenges. Mol Syst Biol. 2007;3:158.

Shah, S. A., et al. "Protospacer recognition motifs: mixed identities and functional diversity." RNA biology 10.5 (2013):891-899.

Shin, J. et al., "Disabling Cas9 by an anti-CRISPR DNA mimic", Science Advances, Jul. 2017, vol. 3, No. 7, article e1701620, 9 pages DOI:10.1126/sciadv.1701620.

Sudres, M. et al., "MyD88 Signaling in B Cells Regulates the Production of Th1-dependent Antibodies to AAV", Molecular Therapy, Aug. 2012, vol. 20, No. 8, pp. 1571-1581 DOI: 10.1038/mt.2012.101.

Swiech L, et al. In vivo interrogation of gene function in the mammalian brain using CRISPR-Cas9. Nat Biotechnol. 2015;33(1):102-6.

Thakore, P. et al., "RNA-guided transcriptional silencing in vivo with S. aureus CRISPR-Cas9 repressors", Nature Communications, Apr. 2018, vol. 9, No. 1674, pp. 1-9 DOI:10.1038/s41467-018-04048-4.

Triantafilou M, et al. Lipopolysaccharide recognition: CD14, TLRs and the LPS-activation cluster. Trends in immunology. 2002;23(6):301-4.

* cited by examiner

CRISPR LOGIC CIRCUITS FOR SAFER AND CONTROLLABLE GENE THERAPIES

CROSS-REFERENCE TO RELATED APPLICATIONS

This application represents the national stage entry of PCT International Application No. PCT/US2018/039583, filed on Jun. 26, 2018, and claims the benefit of U.S. Provisional Application Nos. 62/524,956, filed Jun. 26, 2017, and 62/552,321, filed Aug. 30, 2017, each of which is hereby incorporated by reference in its entirety for all purposes.

BACKGROUND

While genomic research has identified a number of genetic therapy targets that can modify the course of disease, there has been limited translation of genetic therapies into clinical use. For example, current gene therapy techniques face challenges to translation including the potential to target incorrect cells, silencing genes over time, difficulty delivering large genes, high manufacturing cost, and the risk of permanently altering a patient's germline DNA. Clustered Regularly Interspaced Short Palindromic Repeat (CRISPR) System has recently revolutionized the field of genome editing. *Streptococcus pyogenes* Cas9 protein can be targeted to any DNA sequence of interest by means of a small RNA (gRNA) that can be engineered to carry complementary sequences to target DNA. Once at the target, Cas9 protein can either cleave or bind DNA, depending on whether it is catalytically active or null. CRISPR is paving the way to therapeutic and investigational gene editing and modulation in a variety of organisms, including animals and humans. Most CRISPR-based studies have focused on modulating gRNA expression from ubiquitously active promoters. Efforts to generate additional internal regulatory control over CRISPR, such as limitation of cell type-specific CRISPRs, have been limited. Accordingly, there remains a need in the art for safer, controllable CRISPR-based gene therapies for reliable and predictable use in vitro and in vivo.

SUMMARY

Provided herein, in some embodiments, are synthetic CRISPR-based genetic circuits and methods of using the same for spatially and temporally controlled genetic modulation and activation or repression of endogenous gene expression in mammalian cells. These architectures and methods are based, in part, on Clustered Regularly Interspaced Palindromic Repeats (CRISPR) systems. The CRISPR regulatory devices of the present disclosure are spatially and temporally controllable in cells (e.g., human cells).

In a first aspect, provided herein is a synthetic regulatory system for modulating cleavage and transcription in vivo, the system comprising a single amplicon comprising: (a) a nucleotide sequence encoding a multifunctional Cas nuclease; (b) at least two guide RNAs (gRNAs) comprising (i) a first gRNA of 15 or less nucleotides (nt) in length that is complementary to at least a portion of a gene targeted for activation or repression and (ii) a second gRNA of 16 or greater nt in length that is complementary to at least a portion of a nucleic acid targeted for transcriptional modulation, wherein expression of the first gRNA is driven by a promoter comprising a binding sequence for the second gRNA; (c) regulatory control element configured to limit expression of the second gRNA to germ cells; wherein the single amplicon is packaged in a vector for DNA-based viral delivery. The regulatory control element can comprise the second gRNA operably linked to a germ cell-specific promoter. The germ cell specific promoter can be a phosphoglycerate kinase 2 (Pgk2) promoter. The regulatory control element can comprise a ligand-responsive ribozyme comprising a sensor component capable of detecting the presence of a germ cell-specific signal and an actuator component configured for inducible expression of the second gRNA whereby, in the presence of the germ cell-specific signal, expression of the second gRNA recruits the Cas nuclease to the amplicon for cleavage and disruption. The regulatory control element can comprise a ligand-responsive ribozyme comprising a sensor component capable of detecting the presence of a small molecule signal and an actuator component configured for inducible expression of the second gRNA whereby, in the presence of the small molecule signal, expression of the second gRNA recruits the Cas nuclease to the amplicon for cleavage and disruption. The small molecule signal can be selected from the group consisting of doxycycline, theophylline, tetracycline, thiamine pyrophosphate (TPP), S-adenosyl methionine (SAM), Flavin mononucleotide (FMN), P53, and NFκ-b. The first gRNA can comprise a MS2 aptamer target site. The second gRNA can comprise a riboswitch. The promoter comprising a binding sequence for the second gRNA can be a CRISPR-responsive promoter. The CRISPR-responsive promoter can be a CRISPR-repressible promoter (CRP). The CRISPR-responsive promoter can be a CRISPR-activatable promoter (CAP). The second gRNA can be configured to cleave within the Cas nuclease coding sequence. The gene targeted for activation can be a gene associated with tissue repair or wound healing. The gene can be selected from the group consisting of TTN and MIAT. The gene targeted for transcriptional modulation can be selected from the group consisting of ACTC1 and EMX1. The Cas nuclease can be Cas9. The Cas nuclease can be Cas9-VPR. The Cas nuclease can be a *S. aureus* Cas9 nuclease or a *S. pyogenes* Cas9 nuclease. The Cas nuclease can be fused to a functional domain selected from the group consisting of a transcriptional activator, a transcriptional repressor, methyltransferase and a nuclease cleavage domain. The Cas nuclease can be Cas9 fused to a transcriptional activator selected from VPR and a MS2-activator complex. The Cas nuclease can be split Cas9 fused to an activation domain. The vector can be an AAV delivery vector.

In another aspect, provided herein is a synthetic regulatory system for modulating a target gene in vivo comprising (a) a nucleotide sequence encoding a multifunctional Cas nuclease; (b) a first gRNA and a second gRNA, each of 16 or greater nucleotides (nt) in length, wherein the first gRNA is complementary to at least a portion of a target gene, and wherein expression of the first gRNA is driven by a CRISPR-responsive promoter (CRP); and (c) a regulatory control element comprising a ligand-responsive ribozyme comprising a sensor component and an actuator component configured for inducible expression of the second gRNA whereby, in the presence of the small molecule ligand, the target gene is cleaved; wherein the at least two gRNAs and the regulatory control element comprise a single amplicon in a vector for DNA-based viral delivery. The second gRNA can cleave the target gene. The target gene can be proprotein convertase subtilisin/kexin type 9 (PCSK9). The CRISPR-responsive promoter can be a CRISPR-repressible promoter (CRP). The CRISPR-responsive promoter can be a CRISPR-activatable promoter (CAP). The ligand-responsive ribozyme can be induced by a small molecule selected from the group consisting of doxycycline, theophylline, tetracycline, thiamine pyrophosphate (TPP), S-adenosyl methionine (SAM), Flavin mononucleotide (FMN), P53, and NFκ-b. The second gRNA can be configured to cleave within the Cas nuclease coding sequence. The vector can be an AAV delivery vector. The Cas nuclease can be Cas9. The Cas nuclease can be Cas9-VPR. The Cas nuclease can be a *S. aureus* Cas9 nuclease or a *S. pyogenes* Cas9 nuclease.

In a further aspect, provided herein is a method of regulating a nucleic acid based therapeutic agent in vivo, the method comprising introducing the synthetic regulatory system described herein into a cell having a nucleic acid based therapeutic agent, wherein the synthetic regulatory system modulates expression of the nucleic acid based therapeutic agent in the cell upon exposure to an inducer of the inducible promoter. The synthetic regulatory system can be introduced into the cell using one or more DNA viruses.

Figure 1:
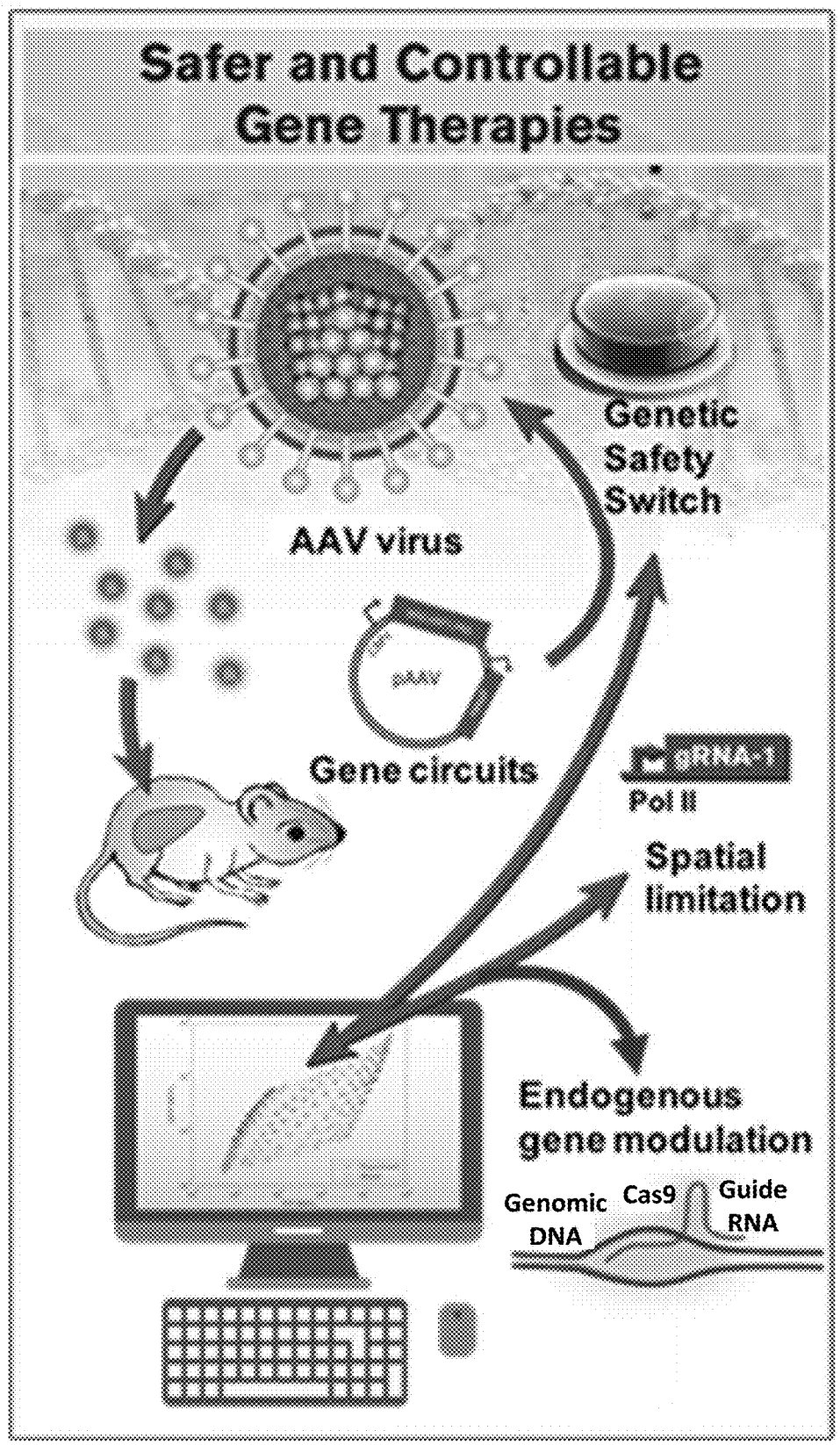
FIG. 1 illustrates use of a CRISPR-based logic gene circuits comprising internal regulatory controls for controlled modulation of Cas9 and gRNA expression or function in vivo and in vitro.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The systems and methods provided herein are based at least in part on the inventors' development of synthetic CRISPR-based genetic circuits useful for spatially and temporally controllable in vivo genome editing and transcriptional modulation. As described herein, the multi-functionality of CRISPR-based genetic circuits makes the systems and methods described herein particularly advantageous for safely controlling endogenous gene expression. Accordingly, provided herein are synthetic CRISPR-based genetic circuits useful for controllable and specific genome editing and transcriptional modulation in vivo.

Synthetic CRISPR-based genetic circuits provided herein are configured to modulate endogenous gene expression in a spatially and temporally controlled manner. Developed using logic-based design principles of synthetic biology and Cas/CRISPR system techniques, the synthetic CRISPR-based genetic circuits described herein limit in vivo expression of gRNAs to tissues or cells of interest, and limit transcriptional modulation via the CRISPR-based system to particular time-points. For example, by embedding an inducible 20-nt gRNA in a synthetic CRISPR-based genetic circuit comprising a 14-nt gRNA (for expression of the 20-nt gRNA under certain cell conditions), the circuit provides a platform for control over the timing of CRISPR functions. In such cases, the circuit employs multiple guide RNAs of different lengths a (e.g., 20-nt and 14-nt gRNAs) and is configured for simultaneous gene activation and repression (disruption) in a single cell. Without being bound by any particular mechanism, theory, or mode of action, the synthetic CRISPR gene circuits described herein exploit the ablation of Cas nuclease activity (e.g., activity of nuclease Cas9) upon binding of the nuclease to a guide RNA (gRNA) having a 14-nt guide sequence rather than a 20-nt guide sequence. Also provided herein are methods for using the systems described herein in genome engineering, e.g. for altering or manipulating the expression of one or more genes or the one or more gene products, in eukaryotic (e.g., mammalian) cells and prokaryotic cells in vitro, in vivo, or ex vivo.

Accordingly, in a first aspect, provided herein is a synthetic regulatory system for modulating cleavage and transcription in vivo. In certain embodiments, the system comprises (a) a nucleotide sequence encoding a multifunctional Cas nuclease; (b) at least two guide RNAs (gRNAs) comprising (i) a first gRNA of 15 of less nucleotides (nt) in length (e.g., a 15-nt gRNA, a 14-nt gRNA, a 13-nt gRNA, a 12-nt gRNA, a 11-nt gRNA, a 10-nt gRNA, etc.) that is complementary to at least a portion of a gene targeted for activation or repression and (ii) a second gRNA of 16 or greater nt in length (e.g., a 16-nt gRNA, a 17-nt gRNA, a 18-nt gRNA, a 19-nt gRNA, a 20-nt gRNA, a 21-nt gRNA, etc.) that is complementary to at least a portion of a gene targeted for transcriptional modulation, wherein expression of the first gRNA is driven by a promoter comprising a binding sequence for the second gRNA; and (c) a regulatory control element configured to limit expression of the second gRNA to germ cells. Preferably, the at least two gRNAs and the regulatory control element comprise a single amplicon. In certain embodiments, the single amplicon is packaged in a vector for DNA-based viral delivery.

Embedded in the CRISPR-based genetic circuits are layers of ribozyme-based "kill switches" that enable spatiotemporally-controlled transcriptional modulation and gene editing. In particular, synthetic CRISPR-based genetic circuits described herein comprise ligand-responsive ribozyme "kill switches" as a regulatory control element, where the regulatory control element enables safe regulation of gene expression by inactivating Cas nuclease activity under certain conditions and limiting activation or repression of endogenous gene expression to target cell(s) of interest.

In some cases, the regulatory control element comprises a ligand-responsive ribozyme comprising a sensor component capable of detecting the presence of a germ cell-specific signal and an actuator component and an actuator component configured for inducible expression of the second gRNA whereby, in the presence of the germ cell-specific signal, expression of the second gRNA recruits the Cas nuclease to the amplicon for cleavage and disruption.

In other cases, the regulatory control element comprises a ligand-responsive ribozyme comprising a sensor component capable of detecting the presence of a small molecule signal and an actuator component configured for inducible expression of the second gRNA whereby, in the presence of the small molecule signal, expression of the second gRNA recruits the Cas nuclease to the amplicon for cleavage and disruption. Exemplary small molecule signals include, without limitation, doxycycline, theophylline, tetracycline, thiamine pyrophosphate (TPP), S-adenosyl methionine (SAM), Flavin mononucleotide (FMN), P53, and NFκ-b.

In preferred embodiments, multiple cell type-specific ribozymes and external inducers (e.g., small molecule agents) are used to control where and when a therapeutic synthetic CRISPR-based genetic circuit is functional. Ribozyme devices can function as ligand-responsive genetic switches or ribozyme switches, where ribozyme activity, and thus target RNA and protein levels, are modulated as a function of ligand concentration in the cell. For example, synthetic CRISPR-based genetic circuits of this disclosure can be spatially targeted to limit cleavage or transcriptional modulation to cells of interest (e.g., somatic cells). In some cases, the first ligand responsive ribozyme comprises a sensor responsive to a germ cell signaling molecule (a molecule found only in germ cells), whereby, in the presence of the germ cell-specific signal, the actuator promotes expression of a second (20 nt) gRNA and, thus, cleavage of the amplicon.

In some cases, a "kill switch" ribozyme comprises a degradation tag (e.g., Small molecule-assisted shutoff (SMASh) domain or other degradation/destabilization domain). In general, degradation/destabilizing domains are small protein domains that are unstable and degraded in the absence of ligand, but whose stability is rescued by binding to a high-affinity cell-permeable ligand. Genetic fusion of a destabilizing domain to a protein of interest results in degradation of the entire fusion. Addition of a ligand for the destabilizing domain protects the fusion from degradation and, in this manner, adds ligand-dependent stability to a protein of interest.

In some cases, it will be advantageous to deliver CRISPR-based genetic circuit at one time point and induce activity of the circuit at a later time point. For example, CRISPR-based genetic circuits could be introduced into one or more cells of a neonate but not activated until a later time point (e.g., particular developmental stage). In such cases, it will be advantageous to configure a CRISPR-based genetic circuit for temporal regulation such that introduction of an inducing agent (e.g., a chemical agent, light-induced agent) can reconstitute, for example, an aptamer-activator complex to modulate an endogenous gene of interest. By way of example, for chemical or light-based induction, an aptamer such as MS2 can be fused with P65-HSF1 and a FKBP-rapamycin binding (FRB) domain or a mutant or variant thereof. In such cases, temporal control is maintained by the addition or removal of small molecule rapamycin (or a rapamycin analog or derivative) at specific time points. In certain embodiments, a ribozyme switch is responsive to a small molecule such as theophylline. In such cases, the presence of theophylline induces a conformational changes in the riboswitch in which the aptamer is bound to theophylline. The RBS is then released and able to promote protein translation.

In preferred embodiments, the CRISPR-based genetic circuit is a single amplicon that can be packaged for in vivo delivery into a mammalian cell using a delivery vector such as an exosome, virus, or viral particle. In certain embodiments, provided herein is a synthetic regulatory system is a single amplicon comprising a multifunctional Cas nuclease, which is in some cases fused to a functional domain, and at least two distinct gRNAs comprising a first gRNA of 15 or less nucleotides in length and a second gRNA of 16 or greater nucleotides in length, wherein the synthetic regulatory system modulates cleavage and/or transcription in a mammalian cell. As used herein, a "guide RNA" (gRNA) is nucleotide sequence that is complementary to at least a portion of a target gene. A gRNA target site also comprises a Protospacer Adjacent Motif (PAM) located immediately downstream from the target site. Examples of PAM sequence are known (see, e.g., Shah et al., *RNA Biology* 10 (5): 891-899, 2013). In some embodiments, the sequence of PAM is dependent upon the species of Cas nuclease used in the architecture.

In certain embodiments, the first (truncated, 14 nt) gRNA is configured to target one or more endogenous genes. By way of example, endogenous genes targeted for activation or repression can include, without limitation, growth factors, cytokines, genes involved in homology directed repair, genes involved in non-homologous end joining (NHEJ), metabolic enzymes, cell cycle progression enzymes, and genes involved in the pathways of wound healing and tissue repair. In some cases, synthetic CRISPR-based genetic circuits of this disclosure are configured to activate expression of one or more of the above-described endogenous genes. In some cases, synthetic CRISPR-based genetic circuits of this disclosure are configured to repress expression of one or more of the above-described endogenous genes.

To improve gene activation/repression effectiveness and scalability of the system, guide RNAs (gRNAs) are in some cases engineered to comprise a minimal hairpin aptamer. In some cases, the aptamer is appended to the tetraloop and stem loop of a gRNA. In some cases, the aptamer is capable of binding to the dimerized MS2 bacteriophage coat proteins. By fusing MS2 proteins with various activators such as p65 and HSF1 transactivation domains (e.g., MS2-p65-HSF1), a target-specific MS2-mediated gRNA can enhance recruitment of transcription factors to the target gene promoter and Cas complex.

In some cases, one or more gRNAs further comprise one or more RNA recognition motifs such as the MS2 binding motif, the COM binding motif, or the PP7 binding motif PP7 to which certain proteins (MS2 coat protein, COM, or PCP, respectively) bind. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. In some cases, the RNA recognition motif (e.g., MS2 binding motif, COM binding motif, or PP7 binding motif) is fused to an activation domain such as, for example, VPR or P65-HSF1. Other transcriptional activators include, without limitation, VP64. P65, HSF1, and MyoD1.

In some embodiments, one or more of the gRNAs is expression under the control of a RNA Pol II promoter or an RNA Pol II promoter. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1α promoter. In some cases, CRISPR-responsive promoters are used. As used herein, the term "CRISPR-responsive promoter" encompasses eukaryotic promoters as well as synthetic gene regulatory devices and circuits for regulated gene expression. In some embodiments, a CRISPR-responsive promoter comprises a RNA Pol II promoter or an RNA Pol II promoter. The CRISPR-responsive promoter can be a CRISPR-repressible promoter (CRP) or a CRISPR-activatable promoter (CAP).

Standard Pol III promoters, such as U6 and H1, which have been used to express gRNAs and short hairpin RNAs (shRNA), do not allow spatial or temporal control of downstream genes. Spatial limitation of CRISPR gRNAs have several important benefits, particularly with regards to human therapeutics: 1) limiting gRNA expression to tissue/cell type of interest, which eliminates the concern that delivery tools distribute the CRISPR coding cassette systematically; 2) avoiding germline mutations by eliminating concern over CRISPR activity in germ cells; 3) differential gene editing/modulation in neighboring or cross-talking cells: gRNA regulation by distinct cell type-specific promoters enables scientists to modulate the expression of different set of genes in distinct cell types. Accordingly, certain embodiments, the CRISPR-based genetic circuit is configured to drive expression of a guide RNA (gRNA) using a cell type-specific promoter. In some cases, a CRISPR-based genetic circuit is configured to comprise an endogenous or cell type-specific promoter in place of a synthetic promoter. For example, a synthetic RNA Pol II or Pol III promoter can be swapped with a cell type- or context-specific promoter and interfaced with intracellular signaling, enabling multi-step sensing and modulation of cellular behavior. In some cases, a transcriptional repression cascade comprises two, three, or four interconnected CRISPR transcriptional repression circuits (NAND logic gates).

A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb).

In certain embodiments, gRNA expression from RNA pol II promoters can be modulated using Csy4 endoribonuclease-mediated cleavage. In some cases, multiple gRNAs are placed in tandem from a single coding region processed by Csy4. In some cases, high ON/OFF ratios are achieved by using a modified U6-driven 14-nt gRNA cassette, where 20-nt gRNA target sites are inserted within both the U6 promoter site and body of the gRNA. This structure forms a second generation kill switch which enables full destruction of the 14-nt gRNA cassette upon expression of 20-nt gRNAs in vitro, in vivo, and ex vivo. In some cases, such kill switches are expressed in vivo in, for example, a mouse liver, which is a frequent target in gene therapy and a tolerogenic immune environment.

In some embodiments, multifunctional Cas nuclease is encoded from an engineered nucleic acid. For example, in certain embodiments, transcriptional modifiers are fused to a multifunctional Cas nuclease to enable site-specific transcriptional modifications. Various strategies can be used to engineer such fusion molecules. In some cases, transcriptional modulators are directly fused to a multifunctional Cas nuclease. In other cases, the modulator is fused to another RNA binding protein such as MS2 bacteriophage coat protein in order to recruit the modulator to the Cas/gRNA/DNA complex.

In some cases, the multifunctional Cas nuclease is fused to an activation or repression domain. In other cases, repression is achieved without the use of any repression domain but, rather, through Cas nuclease-mediated steric hindrance. The repression domain can comprise an aptamer sequence (e.g., MS2) fused to a repression domain such as, for example, a Kruppel associated box (KRAB) domain. Other repression domains include, without limitation, a methyl-CpG (mCpG) binding domain (e.g., binding domain for MeCP2) and KRAB-MeCP2.

The components of synthetic regulatory circuits described herein are preferably provided in a single amplicon. In some cases, however, the components may be in the form of two or more polynucleotide sequences. In such cases, a synthetic regulatory system can comprise introducing into a single cell two cassettes comprising components of a CRISPR-based genetic circuit, where the first cassette comprises a nucleotide sequence encoding a fusion polypeptide of a multifunctional Cas9 nuclease and a 14-nt gRNA configured for gene modulation, and the second cassette comprises the "safety construct"—a 20-nt controllable gRNA. The first cassette further comprises an inducible promoter driving expression of the fusion polypeptide. In some cases, it will be advantageous to fuse a multifunctional Cas9 nuclease to a reporter polypeptide or other polypeptide of interest (e.g., a therapeutic protein). The reporter polypeptide may be a fluorescent polypeptide such as near infrared fluorescent protein (iRFP) (to monitor Cas9 protein dynamics). In some cases, an activator of the inducible promoter is provided by the cassette comprising the safety construct. Activators can mediate or promote recruitment of polymerase machinery to the CRISPR-Cas complex. The activator can be a zinc-finger protein fused to an activation domain such as a VP16 transcription activation domain or VP64 transcription activation domain. In certain embodiments, orthogonally acting protein-binding RNA aptamers such as MS2 are used for aptamer-mediated recruitment of an activator to the CRISPR-Cas complex. For example, an MS2-VPR fusion protein can be used to aid CRISPR-CAS/14-nt gRNA-mediated gene activation by means of aptamer-mediated recruitment of an activator to the CRISPR-Cas complex. In the presence of an inducer, the safety 20-nt gRNA is expressed, resulting in destruction of the 14-nt gRNA cassette. The synthetic regulatory circuit can be an engineered polynucleotide. As used herein, the terms "engineered nucleic acid" and "engineered polynucleotide" are used interchangeably and refer to a nucleic acid that has been designed and made using known in vitro techniques in the art. In some embodiments, an engineered polynucleotide, also referred to as a circuit herein, is a nucleic acid that is not isolated from the genome of an organism. In some embodiments, the engineered polynucleotide is introduced to a cell, plurality of cells, an organ or an organism to perform diverse functions (e.g., differentiation of cells, as sensors within cells, program a cell to act as a sensor, and delivery of selective cell-based therapies).

In some embodiments, the engineered polynucleotide comprises one or more promoters, such as an inducible promoter, constitutive promoter, or a tissue-specific or cell type-specific promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. In some cases, the cell type specific promoter is a germ cell-specific promoter such as, for example, aphosphoglycerate kinase 2 (Pgk2) promoter. Inducible promoters and inducible systems are known and available from a variety of commercial sources, including, without limitation, Invitrogen, Clontech, and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268: 1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Still other types of inducible promoters which may be useful in this context are those which are regulated by a specific physiological state, e.g., temperature, acute phase, a particular differentiation state of the cell, or in replicating cells only. Non-limiting examples of control elements include promoters, activators, repressor elements, insulators, silencers, response elements, introns, enhancers, transcriptional start sites, termination signals, linkers and poly(A) tails. Any combination of such control elements is contemplated herein (e.g., a promoter and an enhancer).

CRISPR systems belong to different classes, with different repeat patterns, sets of genes, and species ranges. A CRISPR enzyme is typically a type I or III CRISPR enzyme. The CRISPR system is derived advantageously from a type II CRISPR system. The type II CRISPR enzyme may be any Cas enzyme. The terms "Cas" and "CRISPR-associated Cas" are used interchangeably herein. The Cas enzyme can be any naturally-occurring nuclease as well as any chimeras, mutants, homologs, or orthologs. In some embodiments, one or more elements of a CRISPR system is derived from a particular organism comprising an endogenous CRISPR system, such as *Streptococcus pyogenes* (SP) CRISPR systems or *Staphylococcus aureus* (SA) CRISPR systems. The CRISPR system is a type II CRISPR system and the Cas enzyme is Cas9 or a catalytically inactive Cas9 (dCas9). Other non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. A comprehensive review of the Cas protein family is presented in Haft et al. (2005) Computational Biology, *PLoS Comput. Biol.* 1:e60. At least 41 CRISPR-associated (Cas) gene families have been described to date.

It will be understood that the CRISPR-Cas system as described herein is non-naturally occurring in a cell, i.e. engineered or exogenous to the cell. The CRISPR-Cas system as referred to herein has been introduced in a cell. Methods for introducing the CRISPR-Cas system in a cell are known in the art, and are further described herein elsewhere. The cell comprising the CRISPR-Cas system, or having the CRISPR-Cas system introduced, according to the invention comprises or is capable of expressing the individual components of the CRISPR-Cas system to establish a functional CRISPR complex, capable of modifying (such as cleaving) a target DNA sequence. Accordingly, as referred to herein, the cell comprising the CRISPR-Cas system can be a cell comprising the individual components of the CRISPR-Cas system to establish a functional CRISPR complex, capable of modifying (such as cleaving) a target DNA sequence. Alternatively, as referred to herein, and preferably, the cell comprising the CRISPR-Cas system can be a cell comprising one or more nucleic acid molecule encoding the individual components of the CRISPR-Cas system, which can be expressed in the cell to establish a functional CRISPR complex, capable of modifying (such as cleaving) a target DNA sequence.

In some embodiments, a synthetic CRISPR-based genetic circuit as described herein may be introduced into a biological system (e.g., a virus, prokaryotic or eukaryotic cell, zygote, embryo, plant, or animal, e.g., non-human animal). A prokaryotic cell may be a bacterial cell. A eukaryotic cell may be, e.g., a fungal (e.g., yeast), invertebrate (e.g., insect, worm), plant, vertebrate (e.g., mammalian, avian) cell. A mammalian cell may be, e.g., a mouse, rat, non-human primate, or human cell. A cell may be of any type, tissue layer, tissue, or organ of origin. In some embodiments a cell may be, e.g., an immune system cell such as a lymphocyte or macrophage, a fibroblast, a muscle cell, a fat cell, an epithelial cell, or an endothelial cell. A cell may be a member of a cell line, which may be an immortalized mammalian cell line capable of proliferating indefinitely in culture.

To achieve endogenous repression of multiple genes, repression domains are included in both gRNAs. In some cases, the gRNAs further comprise one or more aptamers such as MS2, COM, or PP7 to which certain proteins (MS2 coat protein, COM, or PCP, respectively) bind. The repression domain is fused to the aptamer binding protein and, thus, will be recruited to the Cas9/gRNA complex to achieve repression of transcription of endogenous genes. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously.

To achieve endogenous gene activation, the CRISPR-based genetic circuit comprises an endogenous gene promoter in place of the synthetic promoter and the gRNA comprises an activation domain. The activation domain can comprise an aptamer (e.g., MS2) fused to an activation domain such as, for example, VPR or P65-HSF1. Other transcriptional activators include, without limitation, VP64, P65, HSF1, and MyoD1. In certain embodiments, the genetic circuit is configured to target one or more endogenous genes.

In some cases, SMASh or another degradation/destabilization domain is fused to Cas9 nuclease or SAM proteins. In general, destabilizing domains are small protein domains that are unstable and degraded in the absence of ligand, but whose stability is rescued by binding to a high-affinity cell-permeable ligand. Genetic fusion of a destabilizing domain to a protein of interest results in degradation of the entire fusion. Addition of a ligand for the destabilizing domain protects the fusion from degradation and, in this manner, adds ligand-dependent stability to a protein of interest.

Figure 6:
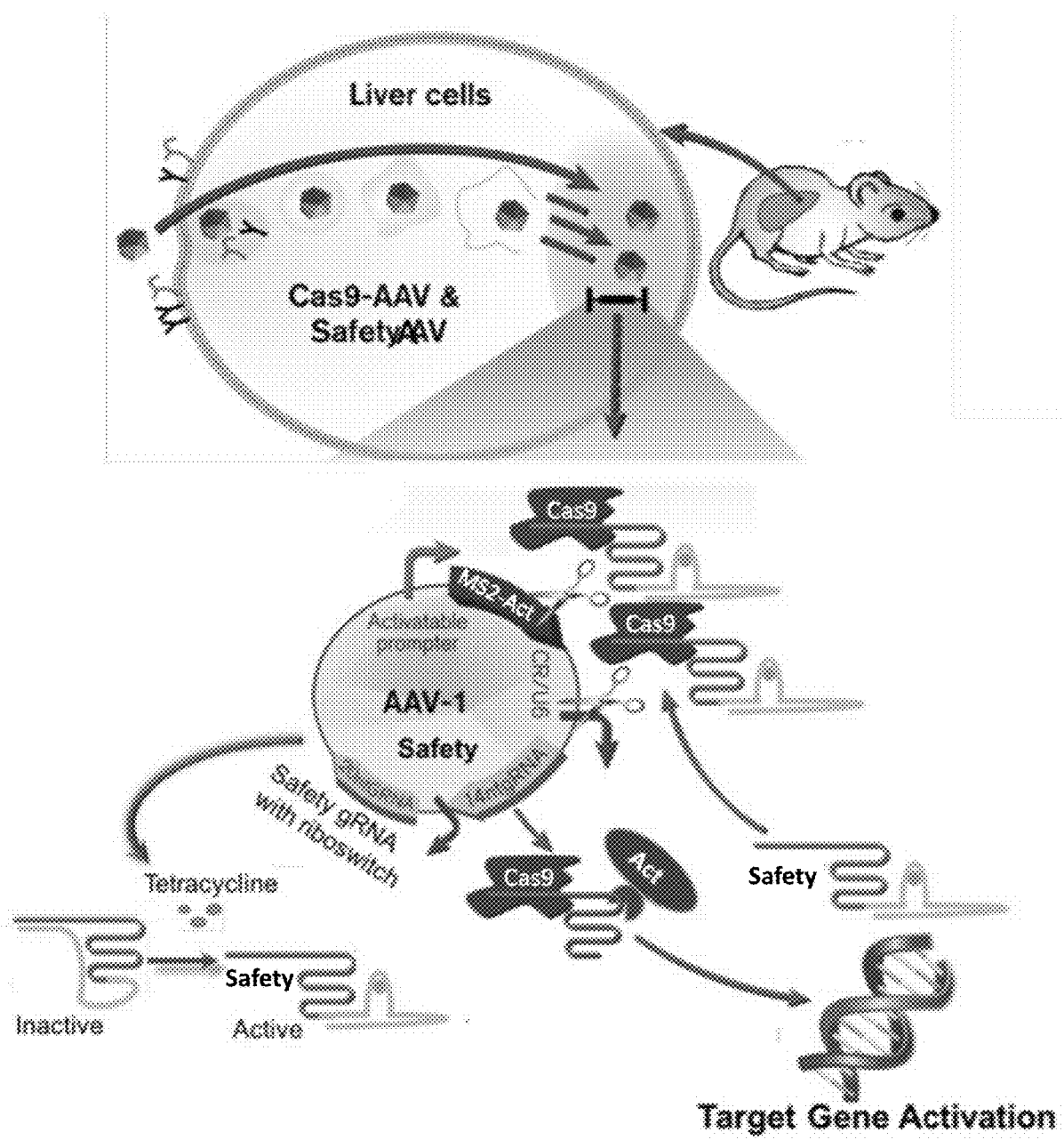
FIG. 6 illustrates an exemplary genetic safety "kill switch."
Figures 7A, 7B:
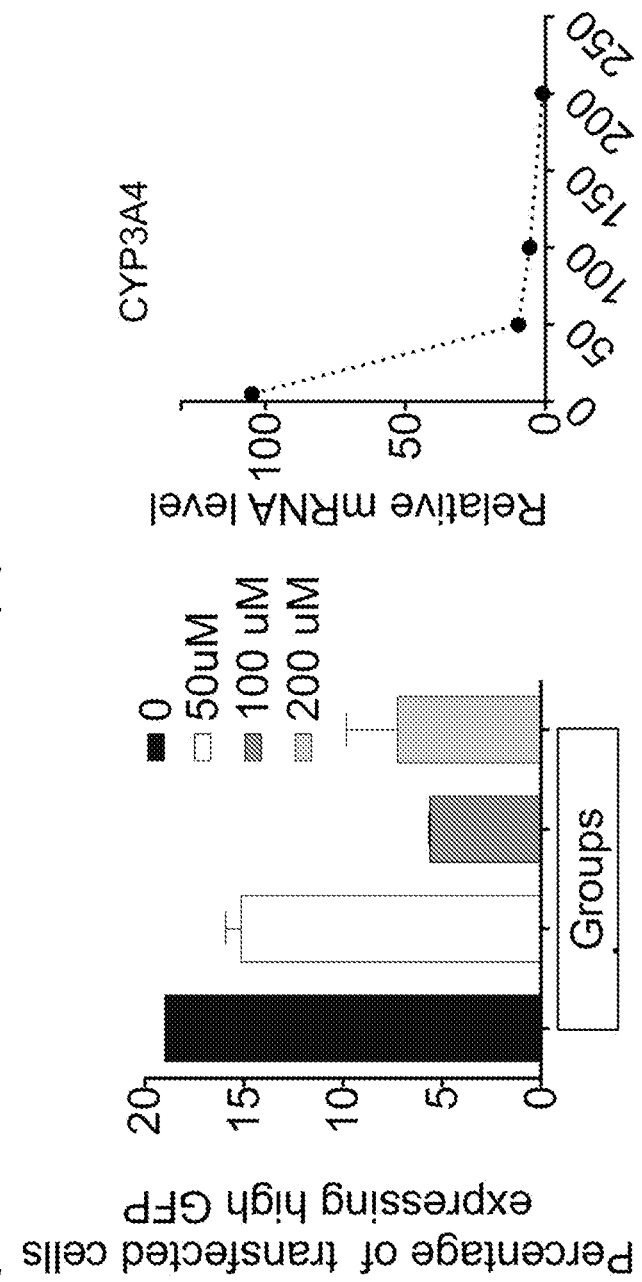
FIG. 7 presents data from a functionality assessment of safety switches in vitro. Assessment of functionality of safety switch in vitro. Tetracycline generates functional 20 nt gRNA, which leads to Cas9/gRNA mediated cleavage within the vector. (a) Flow cytometry shows a decline in GFP protein after 48 hours. (b) qRT-PCR for CYP3A4 RNA level shows reduction in mRNA level after addition of tetracycline.
Figure 8:
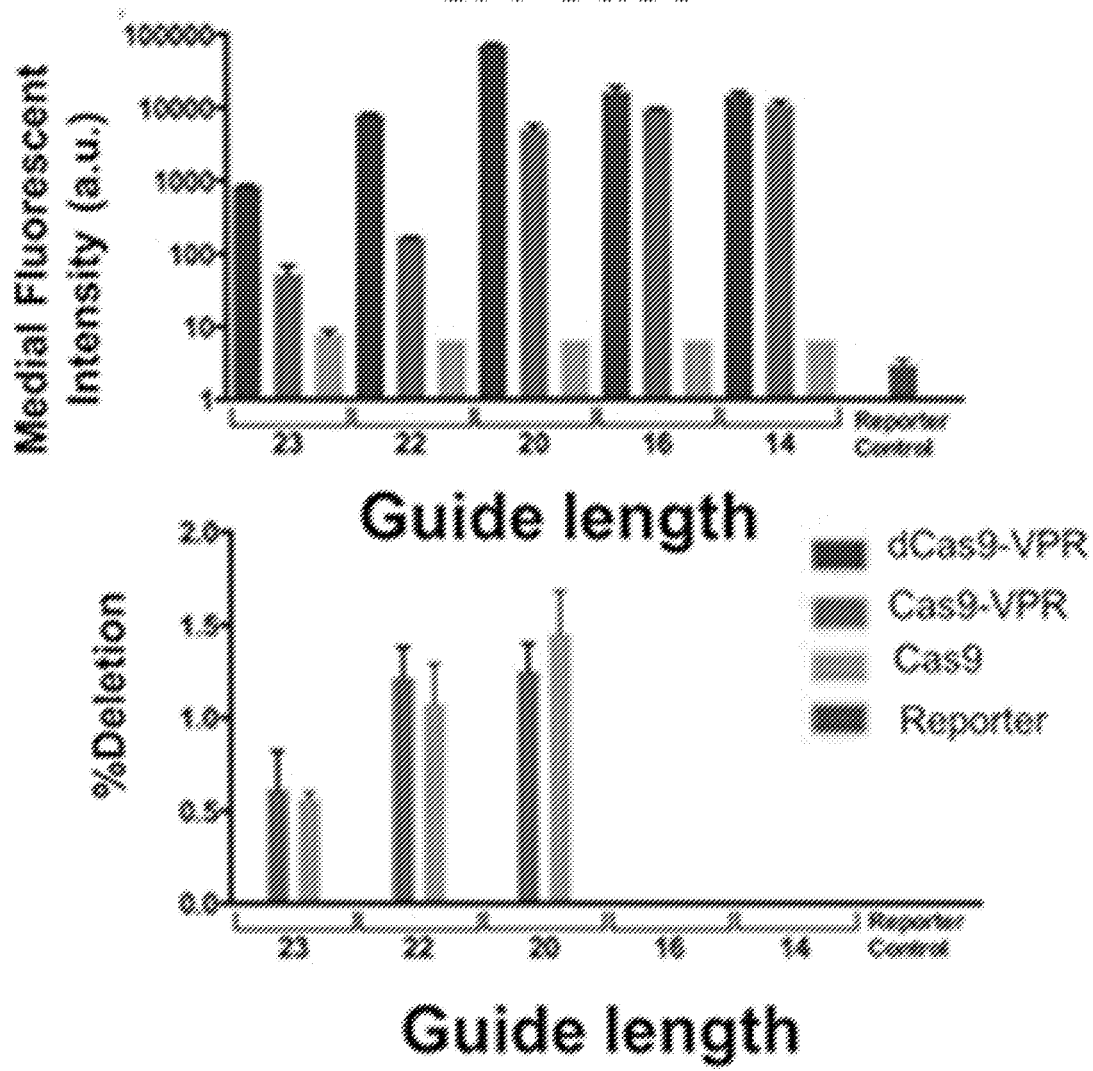
FIG. 8 demonstrates that truncation of gRNAs with SA-Cas9 leads to ablation of Cas9 nuclease activity at 14 nt, and transcriptional activation.

Referring to FIG. 6, one embodiment of a CRISPR-based genetic circuit provided herein is an "Activation-Cleavage (ACL) circuit." ACL circuits comprise a modified U6 (Pol II) promoter comprising safety (20-nt) gRNA target sites within U6 promoter driving truncated gRNAs. Also, 20-nt gRNA target sites are included in the region flanking the constitutive promoter driving MS2-activator complex. This design enables disruption of the expression of 14-nt gRNAs and MS2-activator complex, and disrupts the integrity of the AAV vector upon activation of 20-nt gRNAs. For CRISPR-based transcriptional modulation, the ACL circuit employs (i) an inducible 20-nt gRNA as a safety gRNA to cleave in and disable the amplicon upon addition of an inducer, where the 20 nt gRNA harbors a small molecule inducible riboswitch, and (ii) at least one gRNA of 15 or less nt in length, where this truncated gRNA harbors an RNA binding aptamer fused to activation domain or split Cas9 fusion proteins. The purpose of safety switch is to fine tune level and terminate the function of the delivered viruses.

Cleavage-Cleavage (CCL) circuits are configured to comprise at least two gRNAs of 20 nt length, where one 20 nt gRNA harbors an inducible riboswitch and cleaves within orthogonal target sites within the delivered circuits to temporally fine tune and control this, and the other gRNA cleaves within genomic DNA for NHEJ-mediated or homology-directed repair (HDR)-mediated genetic modulation within the gene of interest. CCL circuits are designed to temporally control CRISPR function and reduce the duration of activity and potentially off target effect. CCL 1.0 has a fluorescent reporter to be used with Cas9 transgenic cell lines/animals. CCL 2.0 includes Cas9 within same vector. These circuits can also include a gRNA of 15 or less nt length to mediate transcription of cell cycle progression enzymes or repression of NHEJ enzyme for enhanced editing. In these cases the circuits should be accommodated within 2 AAV viruses.

In some cases, a viral or plasmid vector system is employed for delivery of a synthetic CRISPR-based genetic circuit described herein. Preferably, the vector is a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via liposomes, nanoparticles, exosomes, microvesicles, or a gene-gun. In certain preferred embodiments, CRISPR-based genetic circuit or components thereof (e.g., gRNAs) are packaged for delivery to a cell in one or more viral delivery vectors. Suitable viral delivery vectors include, without limitation, adeno-viral/adeno-associated viral (AAV) vectors, lentiviral vectors, and Herpes Simplex Virus 1 (HSV-1) vectors. For example, a synthetic CRISPR-based genetic circuit can be introduced into one or more Herpes simplex amplicon vectors.

Viral vectors and viral particles are commonly used viral delivery platforms for gene therapy. Therefore, for faster clinical translation, CRISPR-based genetic circuits described herein can be constructed using embedded kill switches and incorporated into Herpes simplex amplicon vectors. Preferably, a single carrier vector is used to achieve transfection of all synthetic genetic components to target cells. Without being bound to any particular theory or mode of action, it is believed that the ability to control CRISPR functionality, by adding only cleaving 20-nt gRNAs, provide an ideal safety kill switch mechanism due to the small DNA footprint of gRNA and limited pay load capacity of viral particles. In some cases, a Herpes simplex viral delivery system is used for delivery of engineered polynucleotides. In other cases, non-viral particles can be used for delivery. For example, controlled spatial transfection and/or destruction of CRISPR genetic circuits is achieved by assembling and packaging of all CRISPR-based genetic circuit elements in HSV-1 amplicon vectors having large payload capacity (150 kb) and capable of infecting multiple target cells.

Given that DNA cleavage creates irreversible destruction of a gene, this "safety kill switch" mechanism can be effective to permanently shut down the CRISPR genetic circuit, should any adverse effect arise in vivo. However, size of CRISPR system and payload limitation of AAV vectors still necessitates co-administration of two AAV viruses in vivo. Accordingly, in another aspect, provided herein is a co-virus strategy, where the method comprises introducing into a single cell two AAVs. The first virus carries (i) a nucleotide sequence encoding a fusion polypeptide of a Cas9 nuclease, and (ii) a 14-nt gRNA configured for gene modulation. In some cases, the Cas9 nuclease is fused to a reporter polypeptide. The reporter polypeptide may be a fluorescent polypeptide such as near infrared fluorescent protein (iRFP) (to monitor Cas9 protein dynamics). The second virus is the "safety virus" and carries the 20-nt controllable gRNA. To ensure that expression of the Cas9-iRFP fusion polypeptide carried by the first virus occurs only in cells into which both AAVs are introduced, expression of the fusion polypeptide is under the control of an inducible promoter. In some cases, an activator of the inducible promoter is carried by the safety virus. Activators can mediate or promote recruitment of the Pol II machinery to the CRISPR-Cas complex. The activator can be a zinc-finger protein fused to an activation domain such as a VP16 transcription activation domain or VP64 transcription activation domain. In certain embodiments, orthogonally acting protein-binding RNA aptamers such as MS2 are used for aptamer-mediated recruitment of an activator to the CRISPR-Cas complex. For example, the second virus (safety virus) can carry an MS2-VPR fusion protein that aids in CRISPR-CAS and 14-nt gRNA-mediated gene activation by means of aptamer-mediated recruitment of an activator to the CRISPR-Cas complex. In the presence of an inducer, the safety 20-nt gRNA is expressed, resulting in destruction of the 14-nt gRNA cassette.

Applications of the CRISPR-based genetic circuits described herein include, without limitation, in vivo CRISPR-based precision gene therapies for treating chronic and acute conditions in a variety of cell types; a platform of CRISPR cell classifiers can be applied to various cells, tissues, or organs for various therapeutic and/or preventative applications; and in vivo interrogation of endogenous genes using CRISPR activators and repressors, including CRISPR-mediated endogenous gene activation. By way of example, therapeutic applications include, without limitation, treating metabolic resilience in soldiers, improving survival from blood loss, chronic pain management, and enhancing human sensory performance.

Advantageous features of the systems and methods described herein include, without limitation, spatiotemporal limitations on CRISPR functionality via sensing of multiple cellular inputs; simultaneous activation of multiple endogenous genes using Cas9; transcriptional activation by a truncated gRNA (to inactivate Cas9 nuclease) and full-length gRNAs to induce Cas9 nuclease activity; multiple layers of genetic kill switches; use of a single carrier vector to improve transfection of all genetic components to hair cells; and the ability to spatially limit expression of gRNAs to tissues of interest.

So that the compositions, methods, and systems provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

As used herein, the terms "synthetic" and "engineered" are used interchangeably and refer to the aspect of having been manipulated by the hand of man.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

Unless otherwise defined, all terms used in this disclosure, including technical and scientific terms, have the meaning as commonly understood by one of ordinary skill in the art to which this invention belongs.

Although this description refers to certain aspects or embodiments, such aspects or embodiments are illustrative and non-exhaustive in nature. Having reviewed the present disclosure, persons of ordinary skill in the art will readily recognize and appreciate that numerous other possible variations or alternative configurations or aspects are possible and were contemplated within the scope of the present disclosure.

EXAMPLES

The following example demonstrates that by truncating the 5' end of a gRNA and decreasing its target complementary from 20 nucleotides (nt) to 14 nt, it is possible to ablate Cas9 nuclease activity while maintaining its RNA/DNA binding capacity. In our previous work, we set out to develop CRISPR-based genetic NAND gates by placing gRNA target sites within a synthetic promoter framework. This framework allows CRISPR-mediated transcriptional repression of a downstream gene (fluorescent reporter), whereby Cas9 and gRNA combine to act as synthetic transcriptional factors mediating repression. We next employed this genetic NAND gate framework to develop a more complex genetic circuit by layering and interconnecting two gates in a series to form a transcriptional repression cascade. Our primary efforts served as proof-of-concept that CRISPR can be employed for generation of complex genetic circuits.

In our previous work, we also built a small library of gRNA and synthetic promoter pairs and observed a range of transcriptional repression efficiencies in different genetic circuits. gRNAs carrying a 14-nt guide sequence (instead of the conventional 20-nt guide sequence) ablate Cas9 nuclease activity while retaining its DNA binding capacity. Utilizing this design principle, we generated the first multilayer, multi-functional synthetic gene circuits in mammalian cells. Specifically, we generated a number of synthetic genetic safety kill circuits with increasing complexity that regulate and control DNA cleaving and the transcriptional regulation capacity of Cas9-fused to a potent activation domain VPR[35-36] in a logical manner.

Figure 2A:
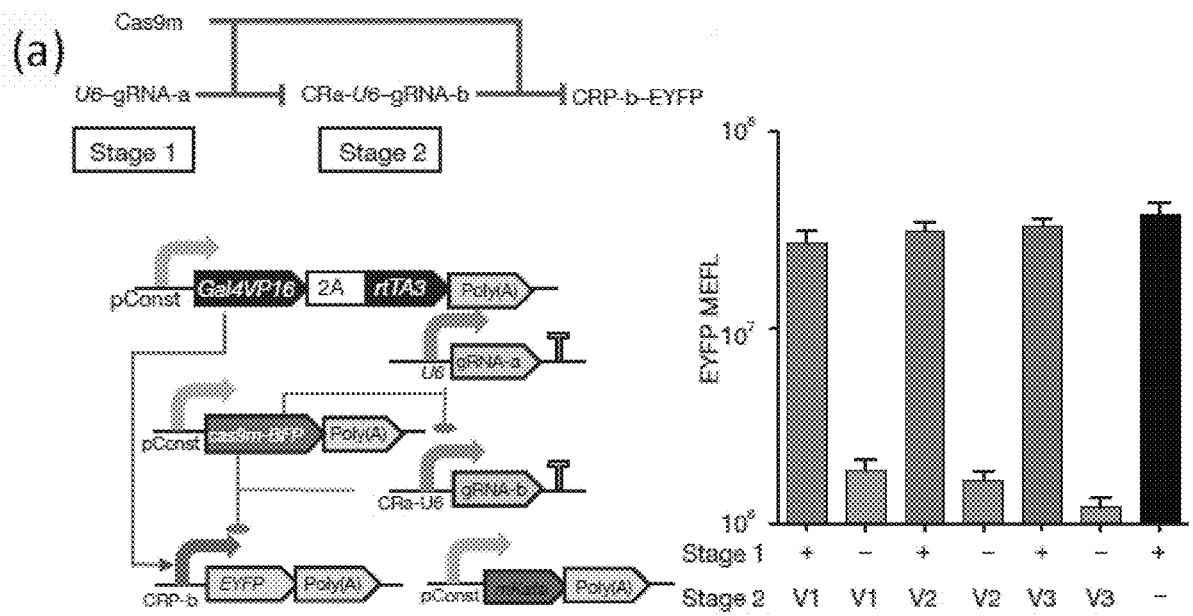
FIGS. 2A-2B illustrates (a) layered cascades of RNA Pol III-driven gRNAs; and (b) layered cascades of Pol III and Pol II-driven gRNAs.
Figure 2B:
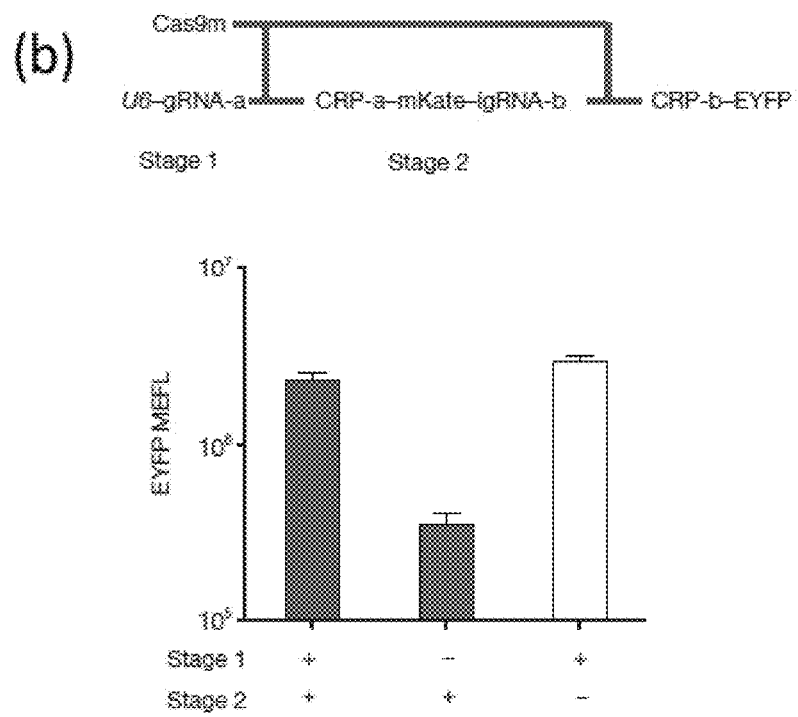
Figures 3A, 3B:
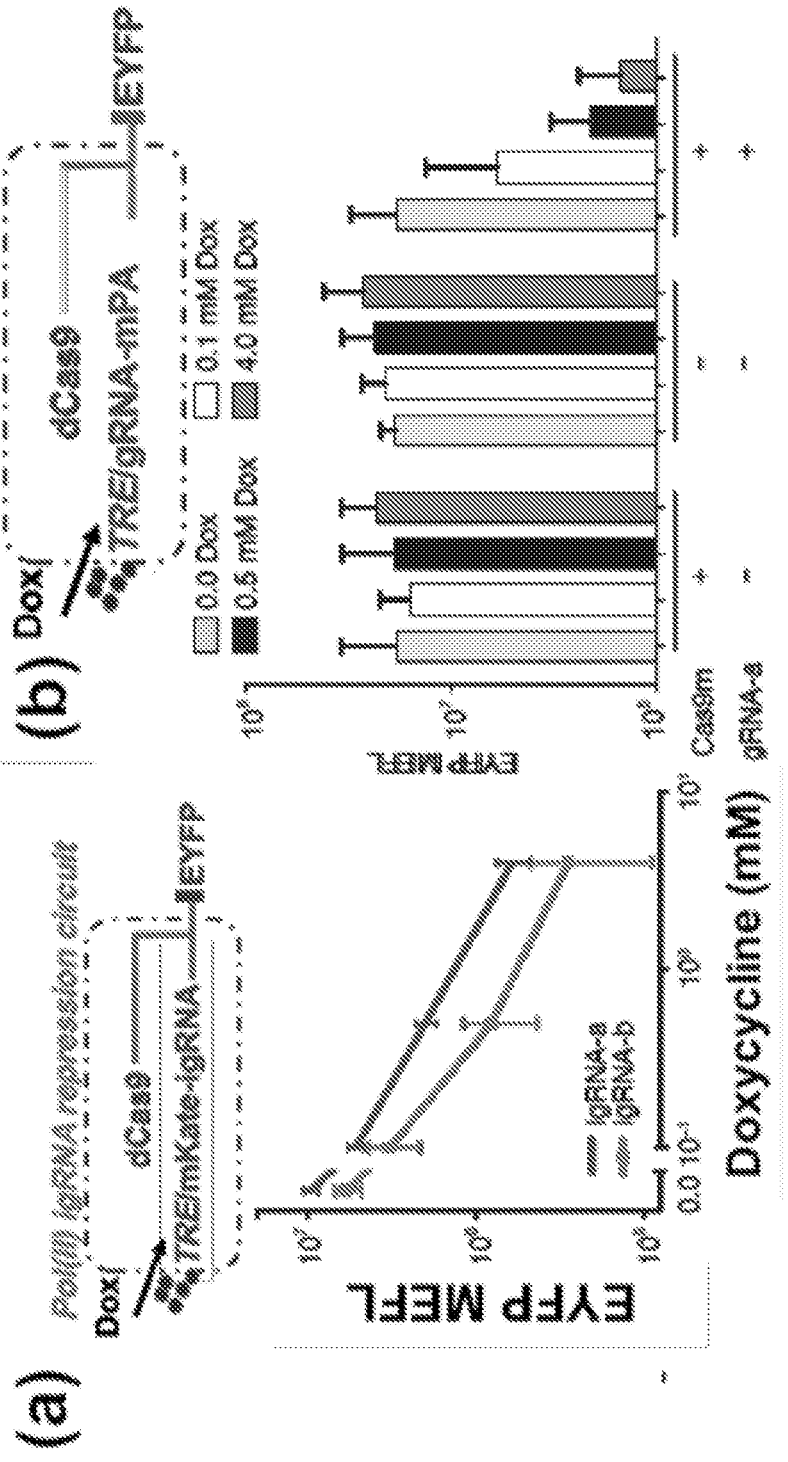
FIGS. 3A-3B demonstrate function of gRNAs expressed from RNA Pol II promoter (TRE), measured by efficiency of repression of an output. (a) gRNA designed as an artificial intron (igRNA); (b) gRNA expressed directly from TRE with minimal Poly A terminator (mPA).

Referring to FIGS. 1A and 1B, we observed that repression efficiencies can be altered by modifying the sequence to which gRNA binds, the location of binding site relative to the TATA box in the promoter, and the number of target sites. As shown in FIG. 1C, the synthetic circuits function independently from each other. These simple transcriptional repression gene tools are building blocks to generate more sophisticated genetic networks in human cells. In some cases, the synthetic CRISPR-based genetic circuit is configured for regulated expression of gRNAs in human cells, using both RNA polymerase type II (RNA Pol II) and modified RNA Pol III promoters. For example, gRNAs can be encoded as artificial introns with flanking splicing sequences within coding sequence of a gene of interest, directly from Pol II promoter with a minimal 3' end poly A sequence or an RNA endonuclease (Csy4)-mediated cleavage of gRNA off a transcribed mRNA. See FIGS. 1d and 1e. With these strategies, we linked gRNA expression to an RNA pol II-based promoter, such as tetracycline response element (TRE). Ultimately, by inserting a gRNA target sequence within an RNA Pol III (e.g., U6), or a Pol II promoter, one gRNA can modulate expression and activity of another gRNA. This enabled us to create multiple layered CRISPR-based transcriptional repression cascades in mammalian cells based on layering two Pol III driven gRNAs (FIG. 2a) or one Pol III- and one Pol II-driven gRNAs (FIG. 2b).

Figures 4A, 4B:
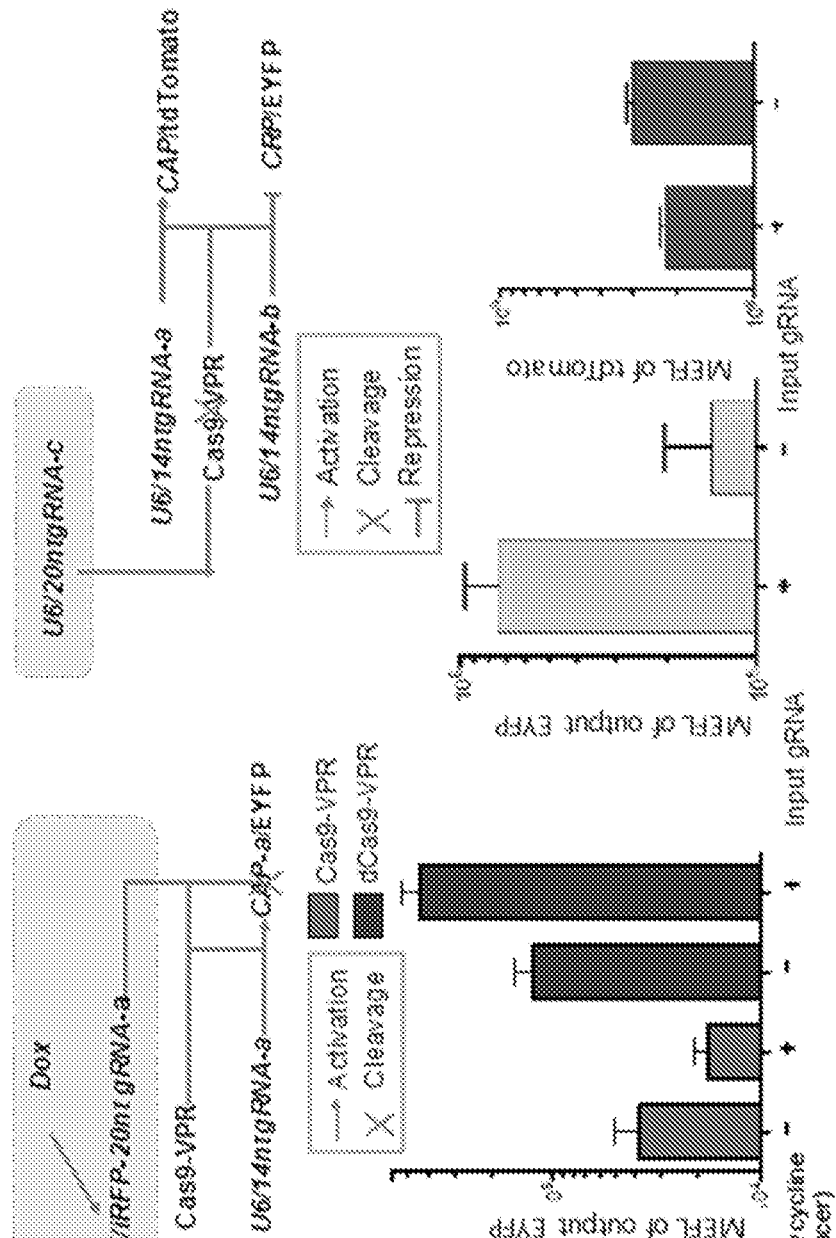
FIG. 4 illustrates exemplary genetic safety "kill" switches having different topologies and complexities. (a) a 20 nt gRNA is induced by Dox, which cleaves within output promoter and reduces 14 ntgRNA/Cas9-VPR mediated activation of output; (b) 20 nt gRNA mediated cleavage occurs within Cas9-VPR coding sequence and reverses 14 nt gRNA activation or repression effects on two different outputs.
Figure 5:
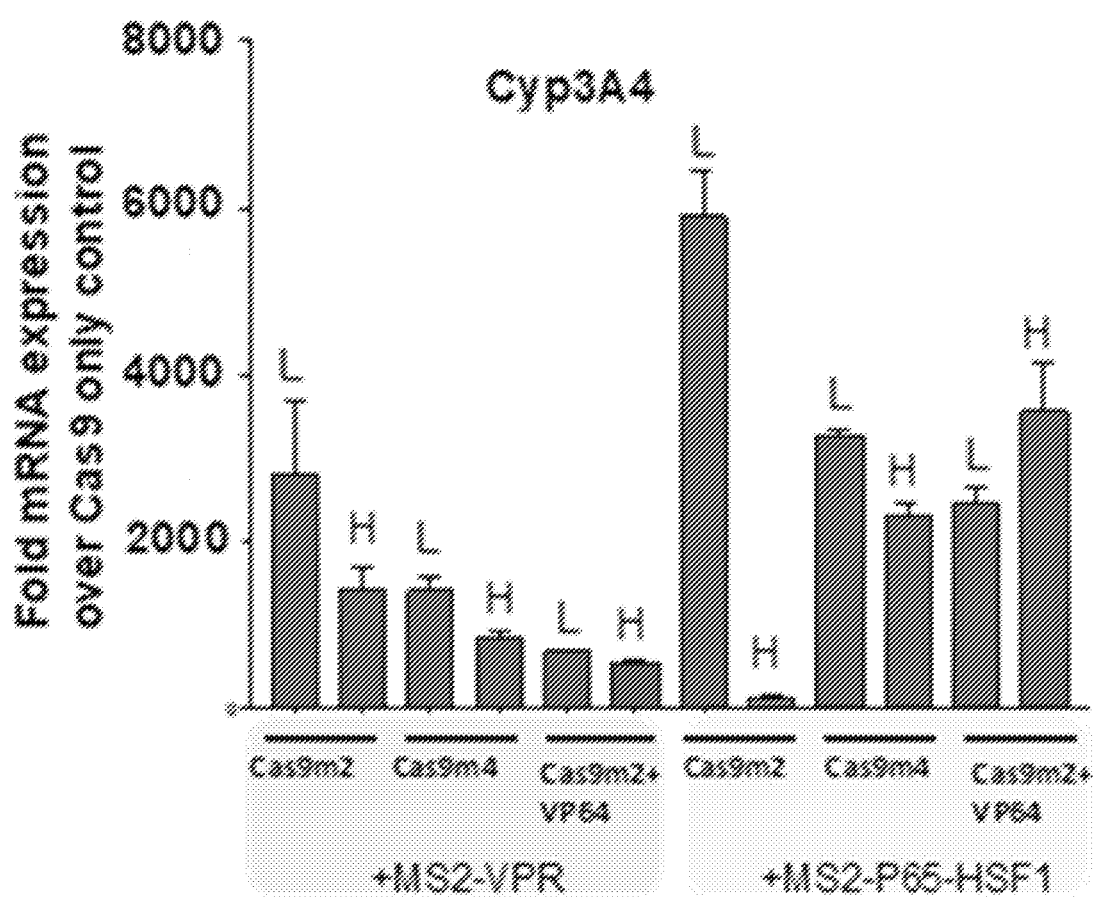
FIG. 5 demonstrates endogenous CYP3A4 activation using different dosage of Cas9/gRNA L (low: 25 ng) and H (high: 200 ng), different Cas9 mutant variant and VPR versus MS2-P65-HSF1 as activators a co-dependent strategy for employing kill switches in vivo.

In one of the circuits illustrated in FIG. 4a, a 14-nt gRNA guides a nuclease competent Cas9-VPR complex to a synthetic promoter that drives an output EYFP expression. A 20-nt gRNA is induced after addition of small molecule doxycycline (DOX), which guides the Cas9-VPR complex to where 14-nt gRNA sits on a synthetic promoter. This leads to cleavage of DNA, destruction of promoter, and reduction in EYFP expression. In another set of genetic kill switches, 20-nt-cleaving gRNAs are designed to cleave within the coding sequence of Cas9-VPR itself, thereby reducing Cas9 expression and its other functionality in activating or repression an output with 14-nt (FIG. 4b). By interconnecting different genetic parts, we also demonstrated the generation of more complex, multilayered genetic kill switch in mammalian cells (FIG. 4c).

Figures 9A, 9B:
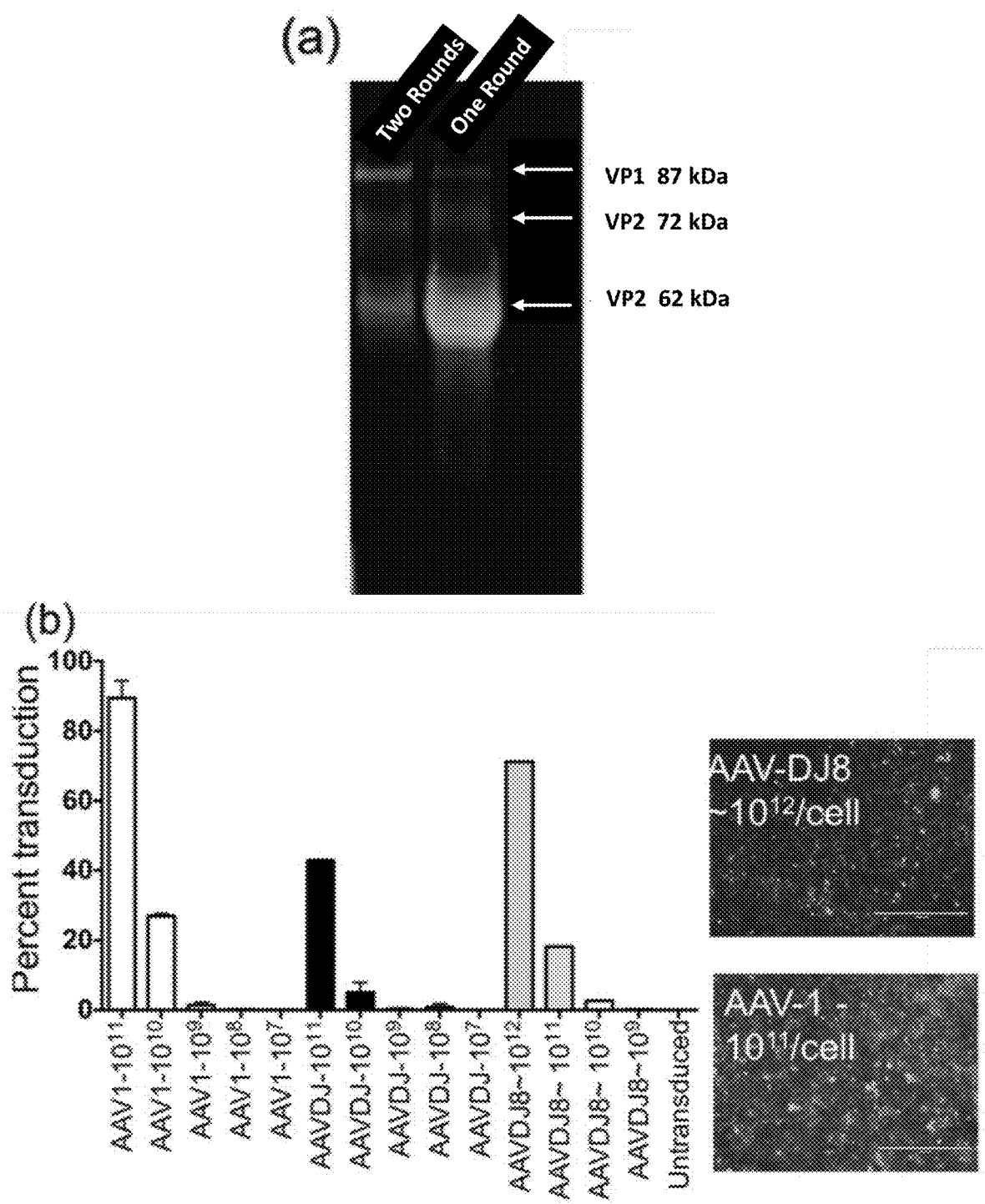
FIGS. 9A-9C demonstrates AAV viral particle purification and cell transduction. (a) Purified AAV-DJ8. (b) in vitro transduction of HEK293 cells with different AAV serotypes and dosages. (c) Purification of mouse hepatocytes and NPCs one week after injection of AAV-1 GFP to WT mice and qRT-PCR for GFP. Results are relative to uninjected WT liver.
Figure 9C:
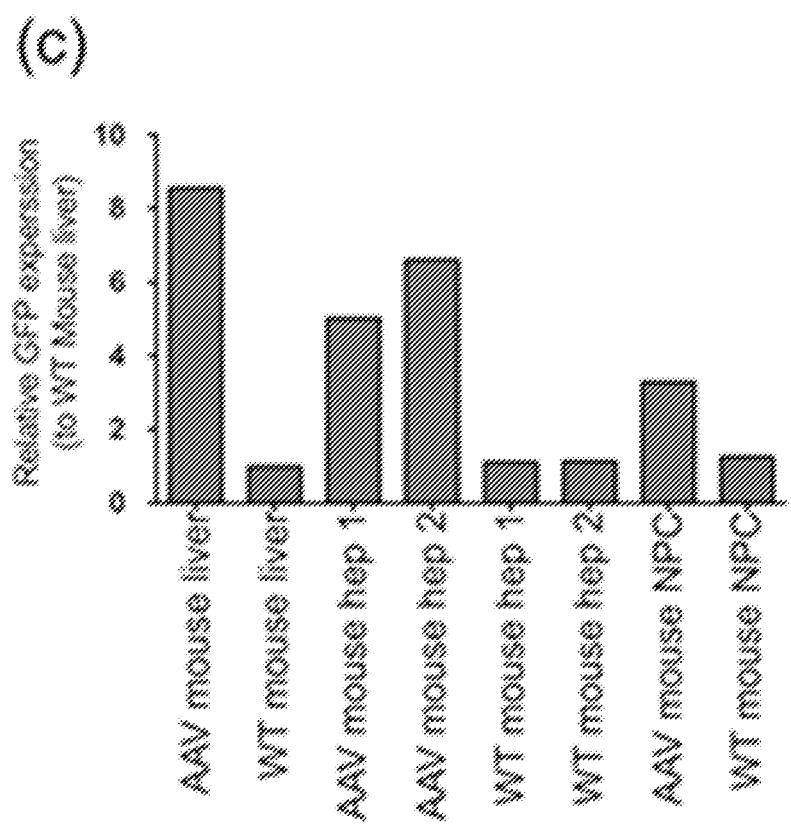

To demonstrate the feasibility of working with liver cells, we injected AAV-1 carrying GFP to C57BL/6J WT mice and after one week, harvested their livers, and purified Heps, and NPCs. Subsequently, we performed qRT-PCR for GFP RNA level and detected GFP expression in all AAV-treated groups as compared to WT control mice (FIG. 9c).

Figures 10A, 10B, 10C:
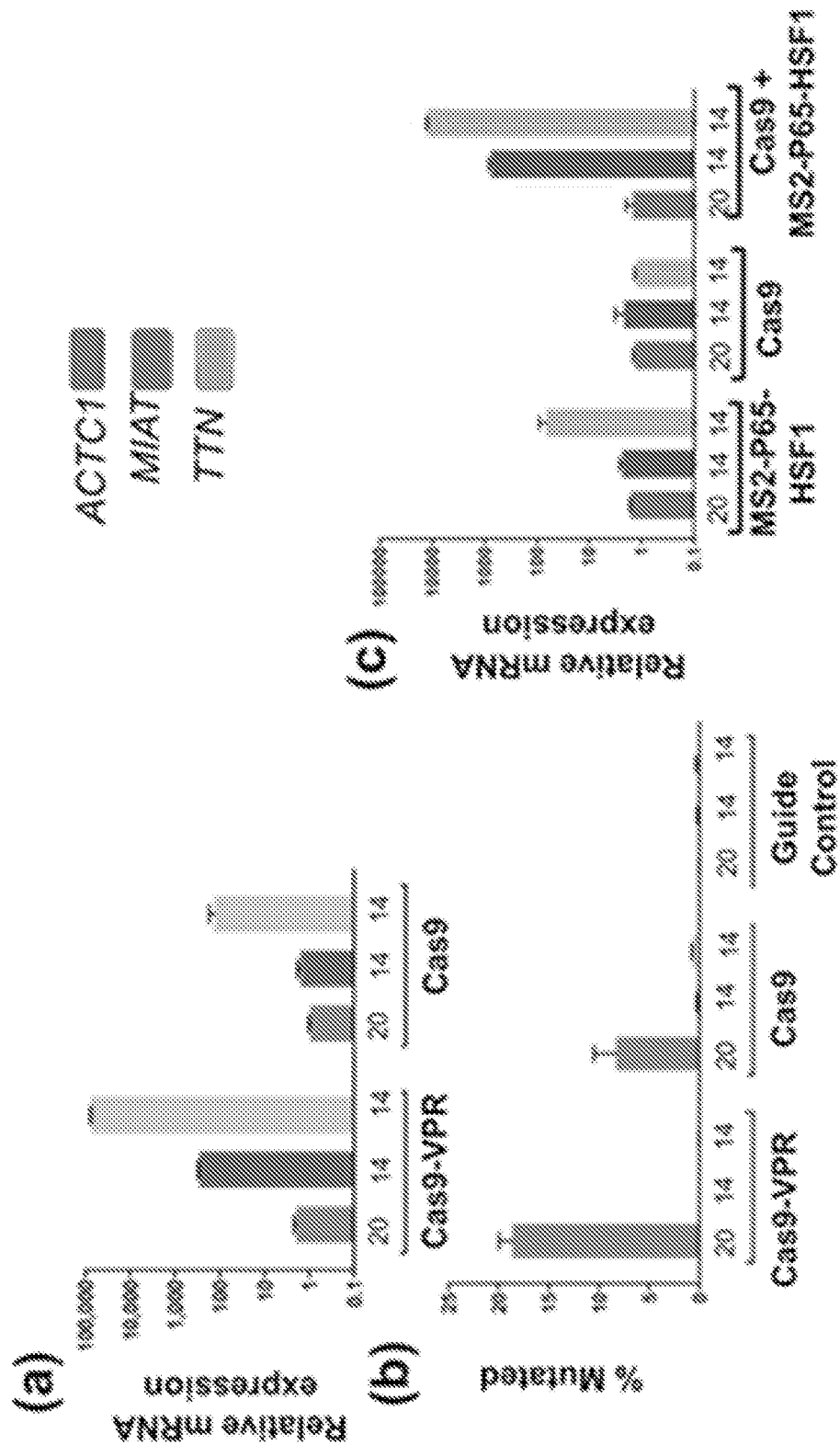
FIGS. 10A-10C demonstrate (a) simultaneous activation and (b) cleavage of endogenous genes using nuclease competent Cas9 protein in fusion with VPR domain and 14 nt gRNAs (for activation of MIAT and TTN) or 20 nt gRNA (for mutation in ACTC1 gene). (c) Aptamer mediated recruitment of an activation domain.

Our studies showed transcriptional modulation by a nuclease-competent Cas9-VPR complex from endogenous and synthetic promoters in mammalian cells. We observed that shorter gRNAs (14-nt guide sequences) ablate Cas9 nuclease activity and can repurpose Cas9 nuclease protein in fusion with an activation domain (VPR) to activate an endogenous gene (FIG. 10a), without detectable DNA cleavage by Cas9 nuclease (FIG. 10b). We also showed activation through an aptamer-mediated recruitment of VPR domain to the complex (FIG. 10c). These findings demonstrate the potential of using Cas9-GFP transgenic mice to reveal design principles of CRISPR mediated gene modulation in vivo without challenges associated with immune reaction to delivery of Cas9 protein that may result in undesirable change to transcriptome in vivo.

Figures 11A, 11B, 11C, 11D:
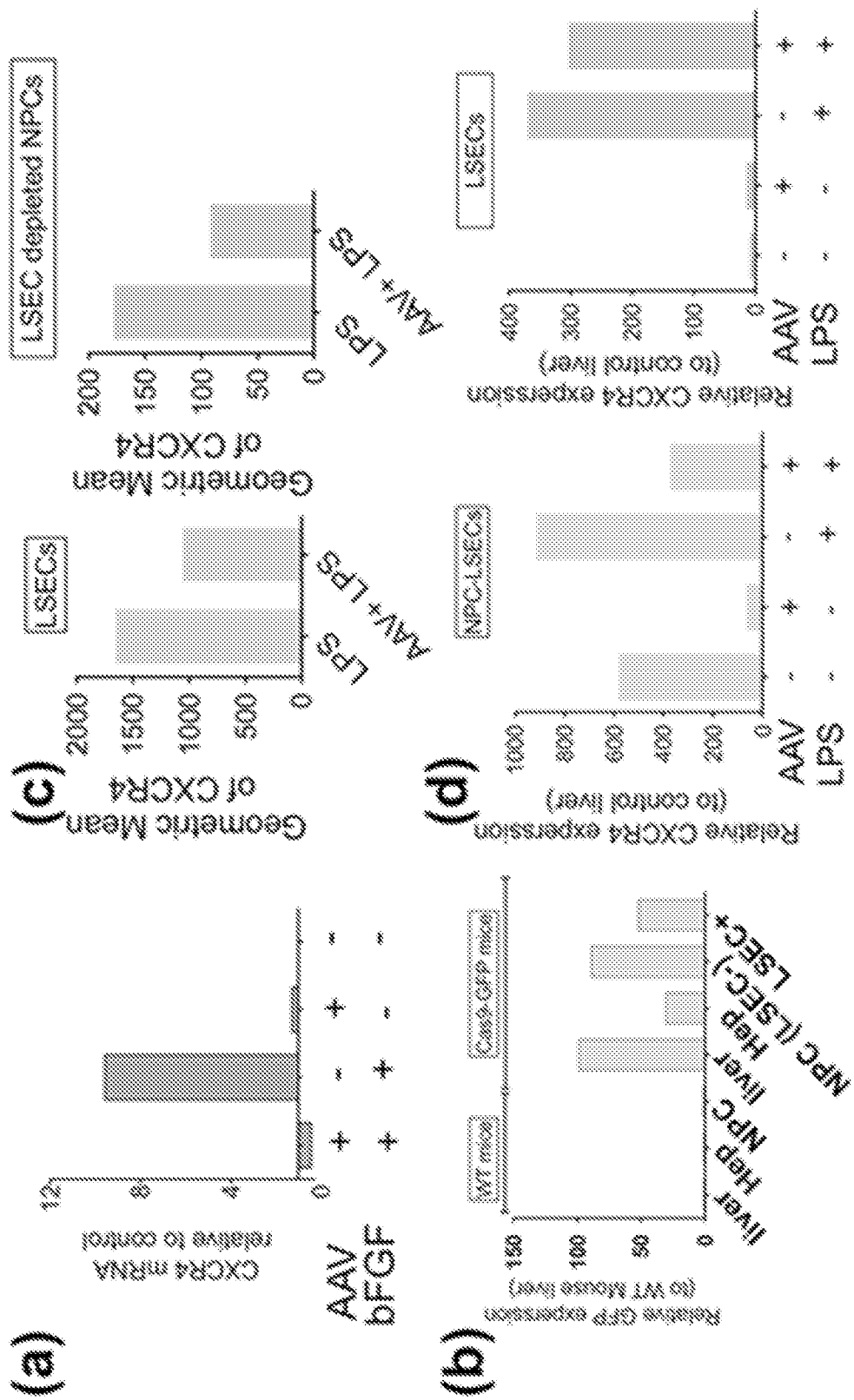
FIGS. 11A-11D demonstrate the effects of CRISPR-based activators and repressors in vivo and in vitro. (a) in vitro validation of AAV-1 CRISPR mediated repression of CXCR4. Values are relative to untreated control (FGF-, AAV-) (b) Analysis of Cas9-GFP expression in different cells isolated from liver of transgenic mice, based on GFP RNA. (c) Flow cytometry analysis of CXCR4 in NPC and LSEC-depleted NPCs isolated from Cas9-GFP transgenic mice, following LPS injection; (d) qRT-PCR analysis of CXCR4 level in NPCs and LSECs isolated from Cas9 transgenic mice in the presence and absence of LPS and AAV-1 CRISPR circuit.

We purified LSECs from Cas9-GFP transgenic mice. 2 days later we transduced the cells in culture with AAV-1 viruses carrying two 14-nt gRNAs against endogenous CXCR4 promoter region as well as MS2 fused with Kruppel associated box (KRAB) and heterochromatin protein 1 a (HP1a) repression domains. We treated cultures with b-fibroblast growth factor (b-FGF), commonly known to induce CXCR4 level in cells, 48 hr later 56. Next, we scarified the cultures after 2 days and performed qRT-PCR analysis of CXCR4 RNA level. Our results demonstrate that AAV-1-CRISPR treated LSECs from Cas9-GFP transgenic mice had significantly lower level of CXCR4 as compared to controls treated with b-FGF, suggesting the CRISPR effect and feasibility of our approach (FIG. 11a).

Informed by in vitro evaluation of selected gRNAs, we will deliver and examine three different CRISPR circuits to transgenic and WT mouse liver in normal condition and following injury (partial hepatectomy, Lipopolysaccharides (LPS)-induced liver damage). To demonstrate feasibility of this approach, we first confirmed Cas9-GFP expression in whole liver, hepatocytes, LSECs, and LSEC-depleted NPCs of transgenic mice by qRT-PCR analysis of GFP level in extracted RNA from samples (FIG. 11b). Next, we performed retro-orbital injection of Cas9-GFP transgenic mice with AAV-1 virus containing MS2-KRAB-HP1a fusion protein and two gRNAs against CXCR4 locus or normal saline. After one week, we injected some groups with LPS (i.p. 5 mg/kg), which has been suggested to modulate CXCR4 expression levels. 48 hours post injection, we sacrificed different mice groups, harvested liver, NPCs and LSECs and performed flow cytometry analysis for CXCR4 protein level on surface of cells (FIG. 11c) and qRT-PCR of CXCR4 RNA level (FIG. 11d). Results demonstrate that LPS injected AAV-1-CRISPR pre-treated mice have lower level of CXCR4 in different sub-populations, suggesting the feasibility of using Cas9-GFP transgenic and truncated gRNA approach.

Figures 12A, 12B:
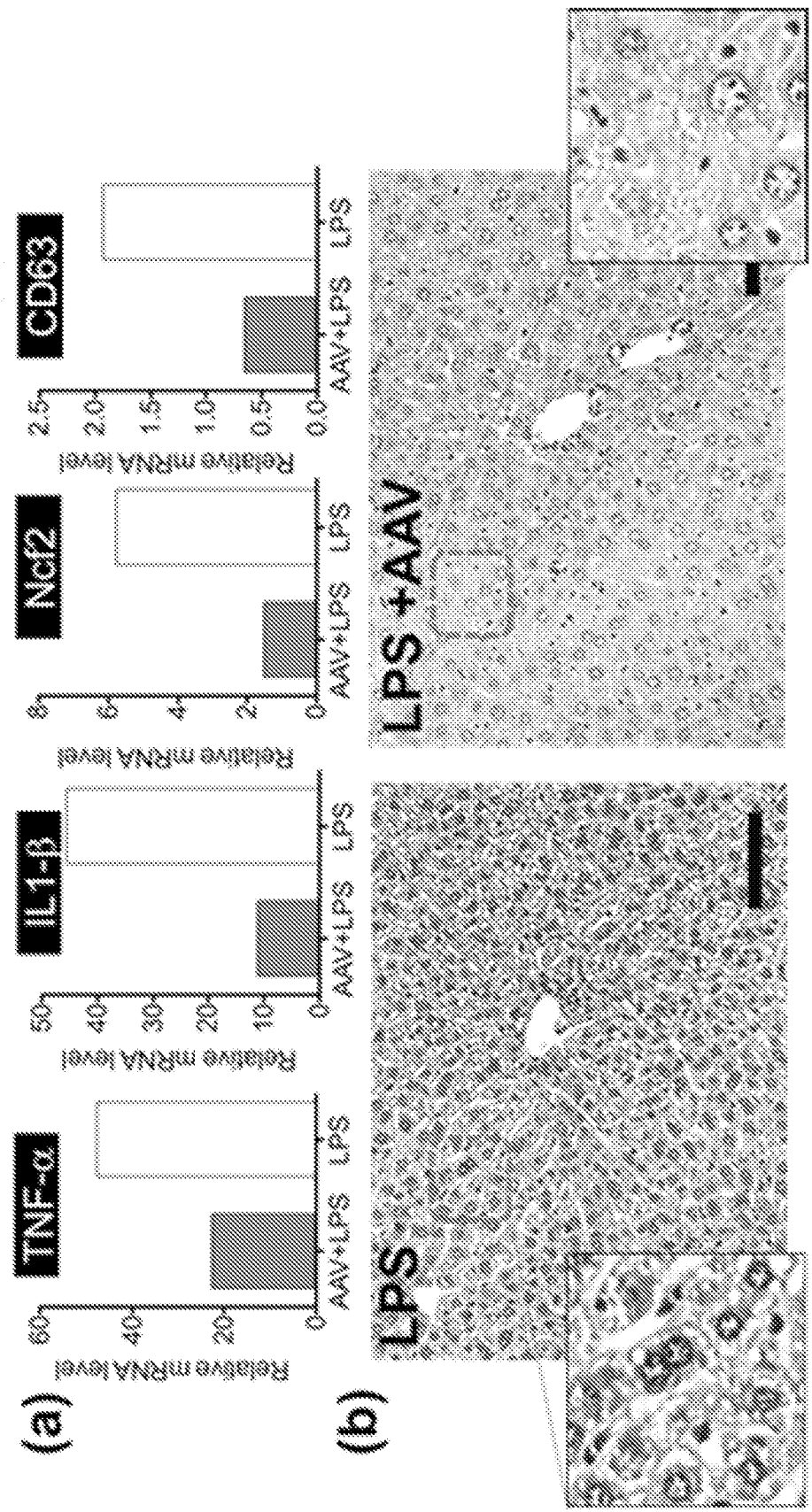
FIGS. 12A-12B demonstrate (a) qRT-PCR of inflammatory cytokines expressed in primary hepatocytes (Heps); and (b) H& E staining of whole liver from treated mice. Images show decreased hepatocyte deformity in CRISPR treated groups. Scale=200 μm.
Figure 13:
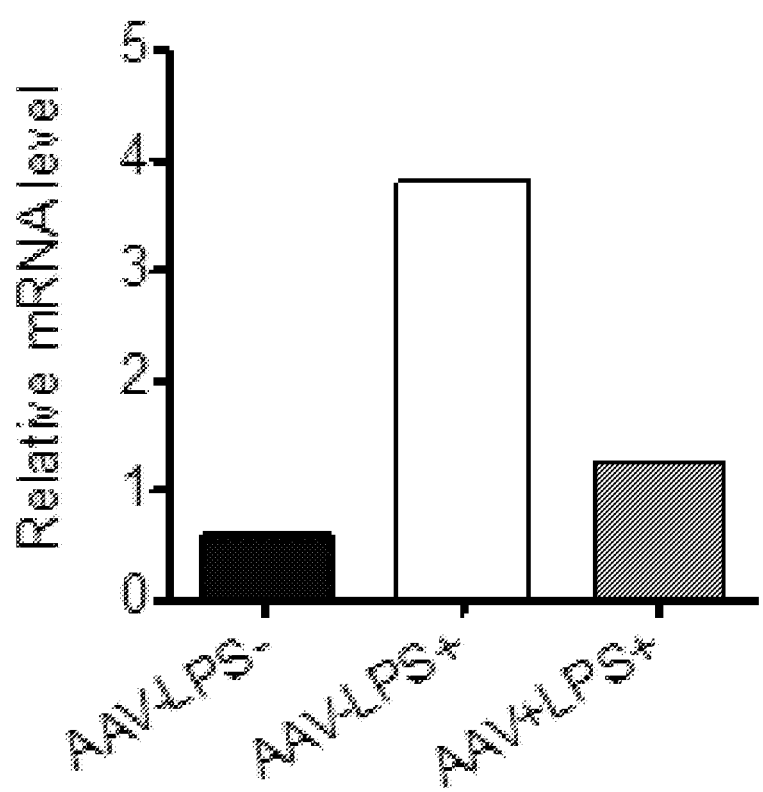
FIG. 13 presents analysis of MyD88 mRNA from primary hepatocytes (Heps) 48 hours after LPS.

We also examined a panel of other inflammatory markers associated with liver inflammation and injury. As shown in FIG. 12a, we demonstrated that demonstrated that AAV/CRISPR treatment reduced the level of markers associated with acute inflammation in primary Heps. To understand the effect of treatment on overall tissue phenotype, we prepared sections of liver for histology and performed H&E staining to investigate tissue structure and hepatocyte morphology. 48 hours after administration of LPS, CRISPR pre-treated groups demonstrated reduced hepatocyte cellular degeneration and damage as compared to the LPS only control group (FIG. 12b). We performed similar experiments targeting mouse MyD88 locus as well, and observed reduction in MyD88 mRNA level in Heps following CRISPR delivery (FIG. 13). These experiments suggest the feasibility of our approach and applicability of Cas9-GFP transgenic mice here.

Figure 14:
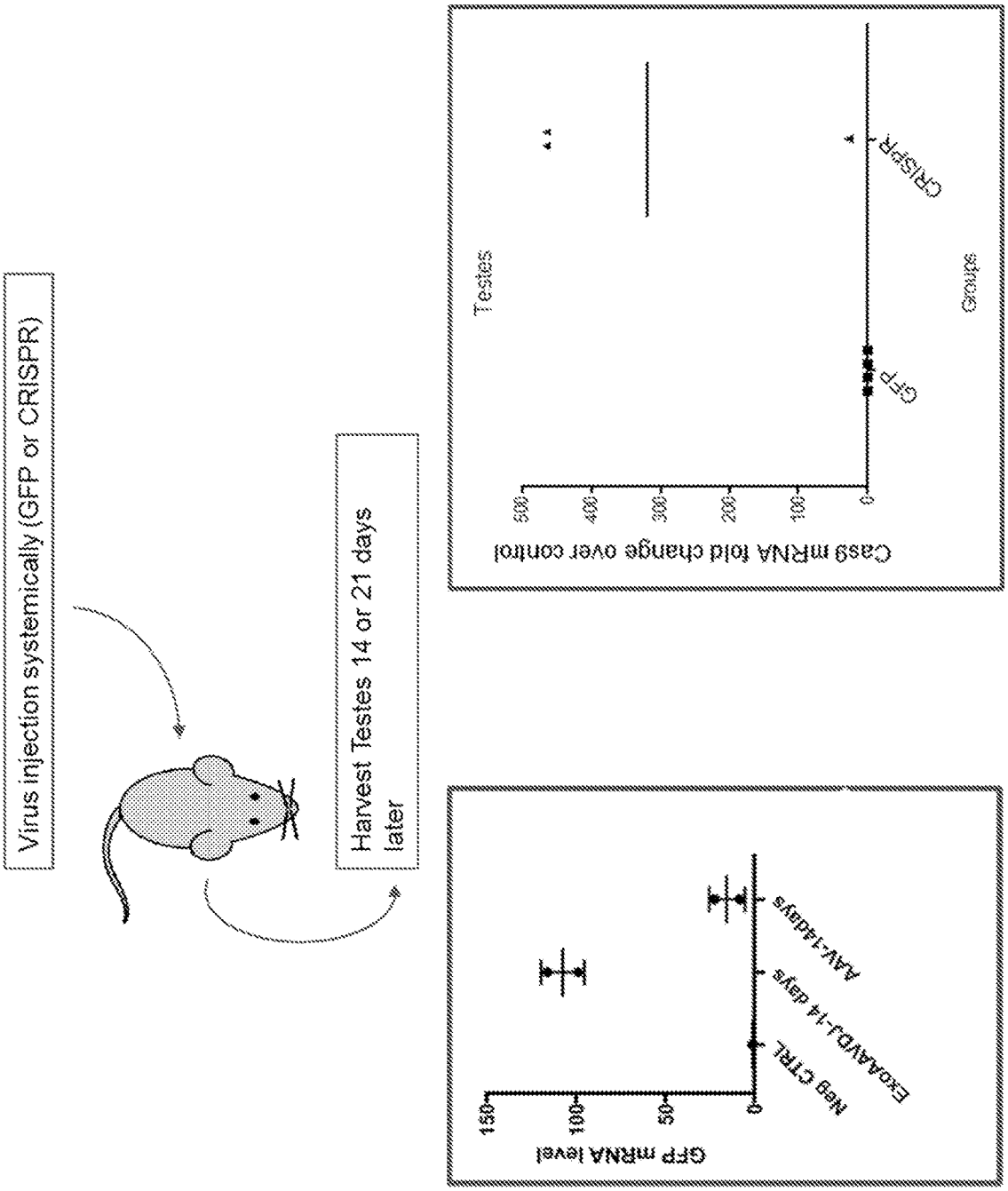
FIG. 14 demonstrates transgene detection in testes following systemic delivery to mice. AAV virus harboring GFP or Cas9 gene was injected to mice systemically. The level of transgene expression in testes was assessed by qPCR 14 days post injection.

Mice were systemically injected with AAV virus harboring GFP or Cas9 gene. 14 days post injection, the level of transgene expression in testes was assessed by qPCR. As shown in FIG. 14, the data demonstrated high GFP and Cas9 expression in testes, which confirmed successful delivery of a transgene to testes via AAVDJ through systemic injection.

Figure 15:
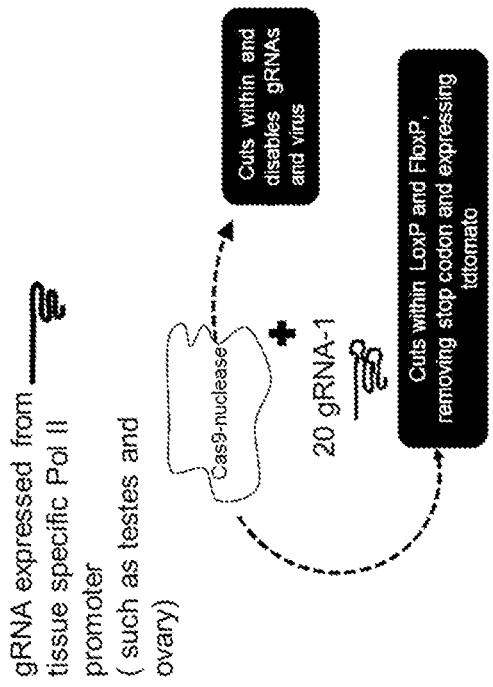
FIG. 15 demonstrates design and testing of safety switches for reproductive organs. AAV virus contained a 20 ntgRNA that was designed to cut within the amplicon as a kill switch is driven by a pol II promoter, which is specific to reproductive tissues. AAV virus also contained gRNAs that cut within Loxp- and Floxp-removing stop codons, leading to tdtomato expression. 14 days post injection, the level of tdtomato expression in testes was assessed by qPCR.
Figure 15:
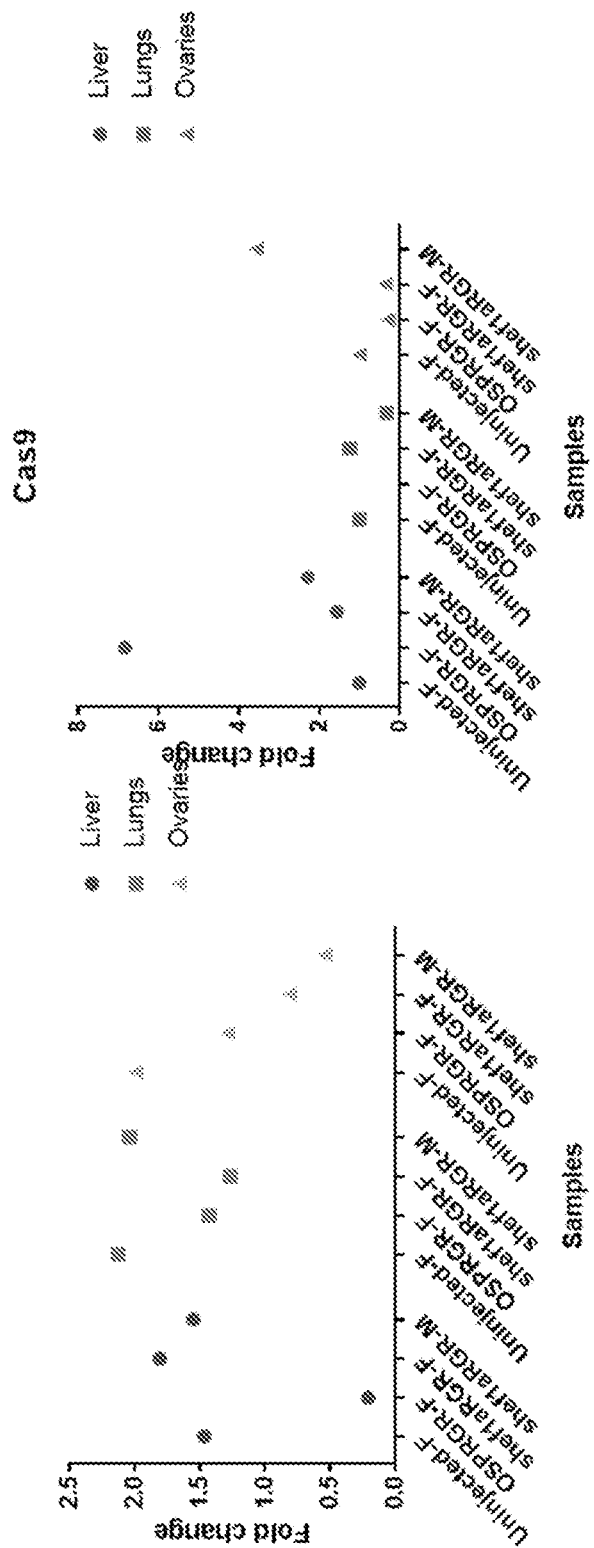
Figures 16A, 16B:
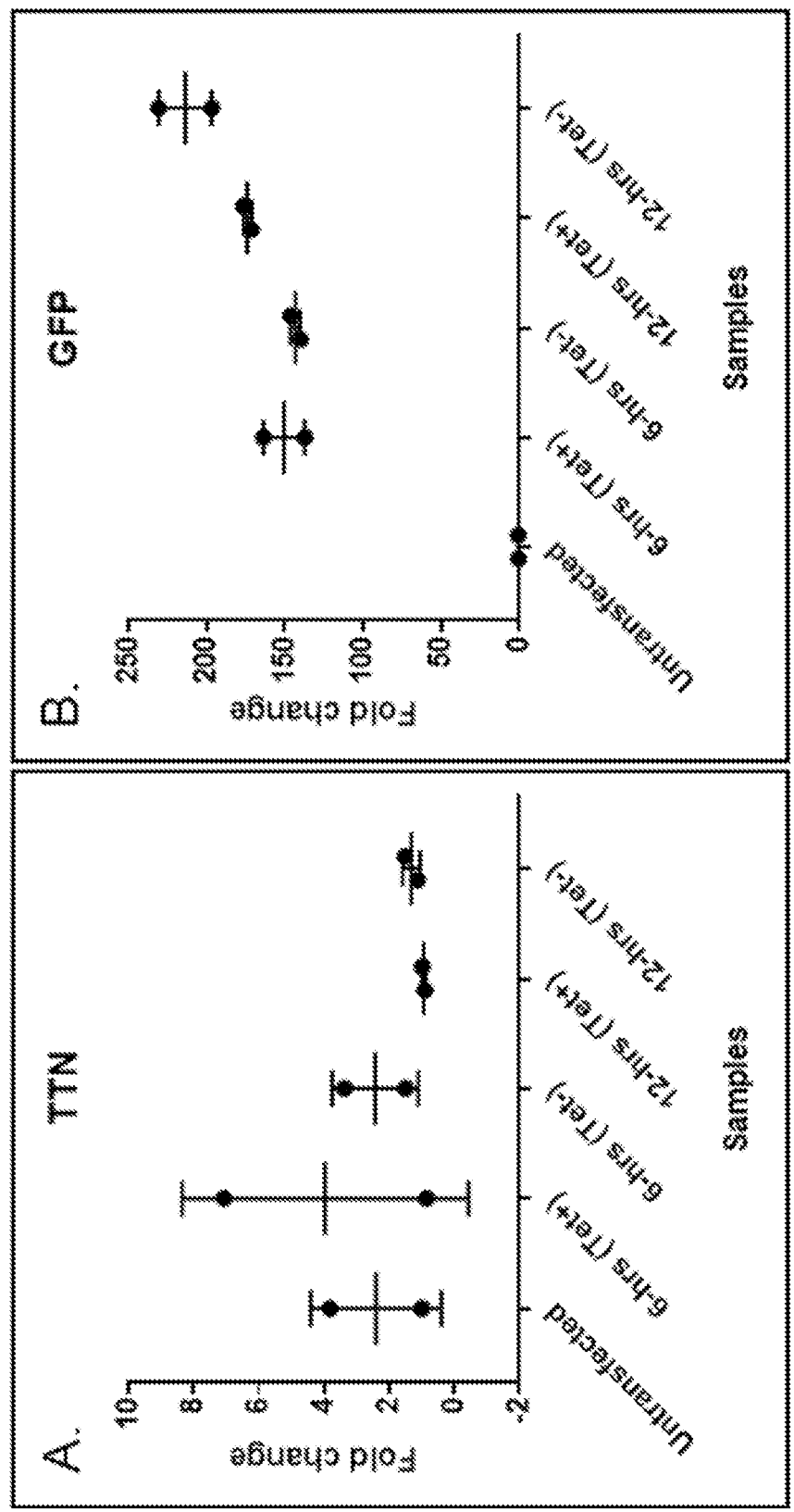
FIGS. 16A-16C demonstrate Design and validation of kill switch in vitro. Neuro-2A cells were transfected with TTN-kill switch constructs, while controls were transfected with GFP. On the next days, tetracycline (tet) was added to the transfected cells to activate the kill switch. Cells were harvested 6 hours and 12 hours post transfection. A and B: qPCR results detecting TTN and GFP mRNA levels showed that GFP expression increased with time. At a 12-hour time point, tet added samples showed lower or equal level of expression of TTN and GFP indicating the functionality of kill switch.
Figure 16C:
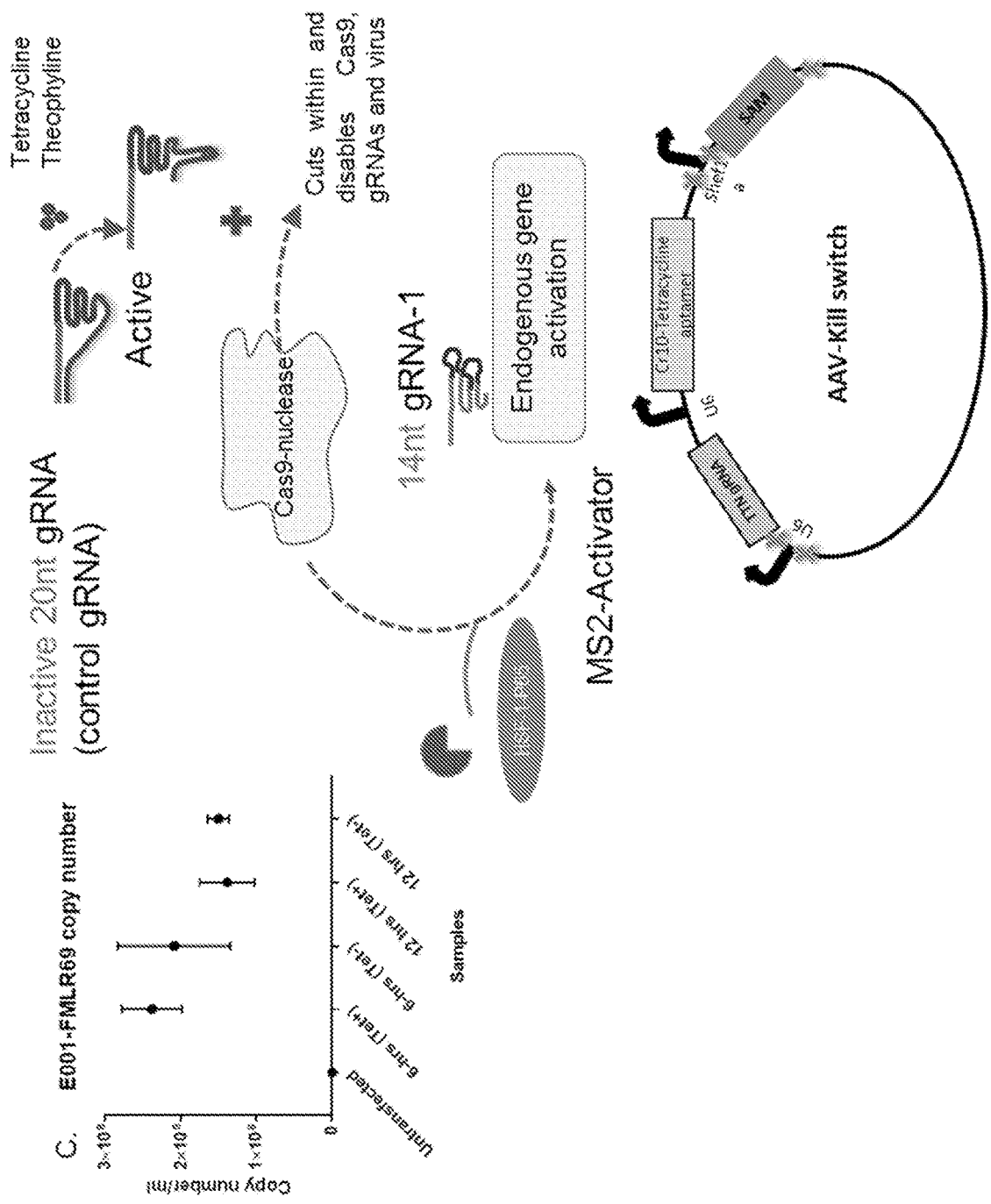

Safety switches were tested in expression in reproductive organs. AAV virus containing a 20 nt gRNA that was designed to cut within the amplicon as a kill switch was driven by a pol II promoter which is specific to reproductive tissues (testes, ovaries). AAV virus also contained gRNAs that cut within Loxp and Floxp, thus removing stop codons and leading to tomato expression. As shown in FIG. 15, tdtomato expression in reproductive tissues was assessed by qPCR. Since these data did not reveal the expected kill switch functionality, we developed another circuit and tested it in vitro (FIG. 16). Neuro-2A cells were transfected with 20-nt gRNA kill switch constructs. Specifically, we engineered an inducible kill switch by fusing a riboswitch that recognizes tetracycline. The circuit also contained a 14 nt gRNA to activate an endogenous gene and a 20 nt gRNA having a target located within the circuit. In the presence of tet, Cas9-nuclease cuts within the amplicon and disables the circuit. At a 12-hour time point, tet added samples showed lower or equal level of expression of TTN and GFP, thus indicating the functionality of the kill switch. As shown in FIG. 16, in vitro data validated the functionality of this kill switch in mouse cells when targeting endogenous TTN expression.

Figure 17:
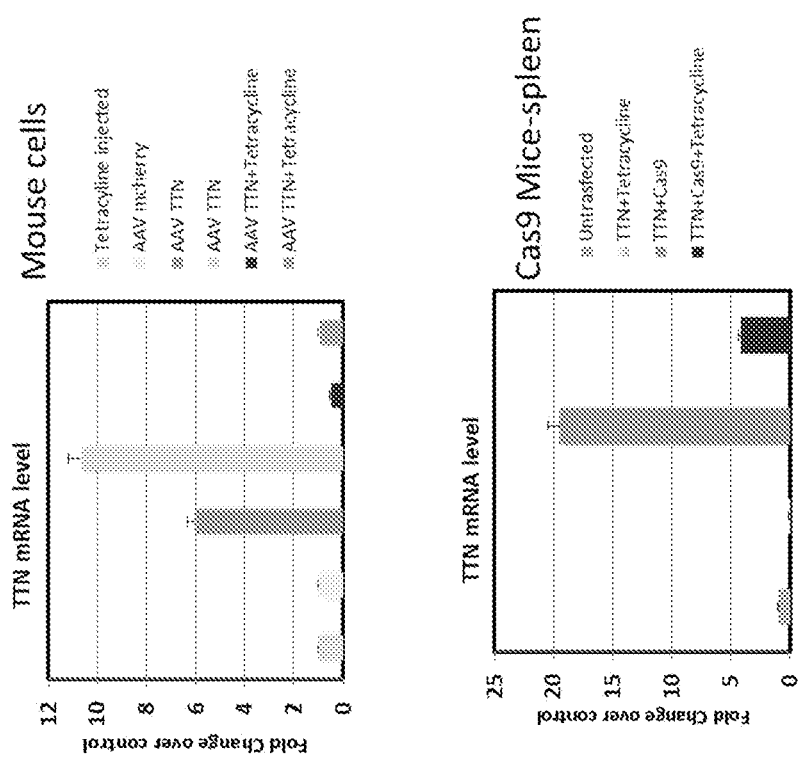
FIG. 17 demonstrates control over CRISPR-mediated gene activation in vivo. As illustrated, an inducible kill switch was produced by fusing a riboswitch that recognizes tetracycline. The resulting circuit contained a 14 nt gRNA to activate an endogenous gene and a 20 nt gRNA that its target is located within the circuit.
Figure 17:
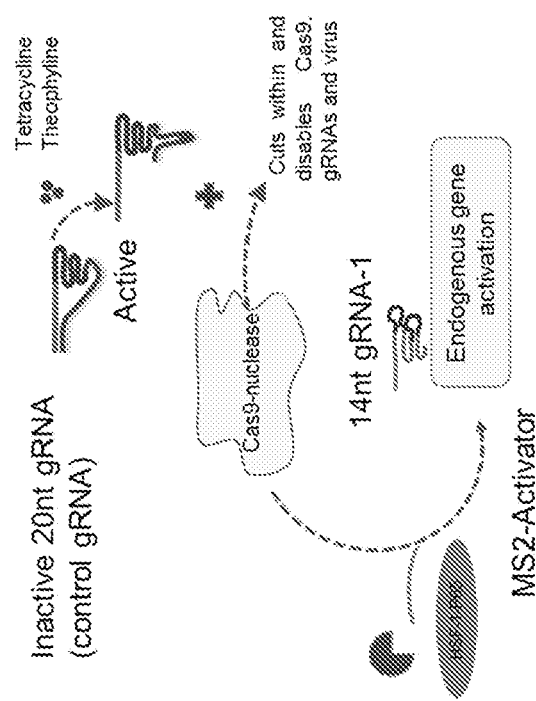

Next, kill switch circuits were tested for the ability control over CRISPR mediated gene activation in vivo. As shown in FIG. 17, the in vivo data demonstrated endogenous activation of TTN in the absence of tetracycline (tet), and disruption of the circuit in presence of tet.

Figure 18A:
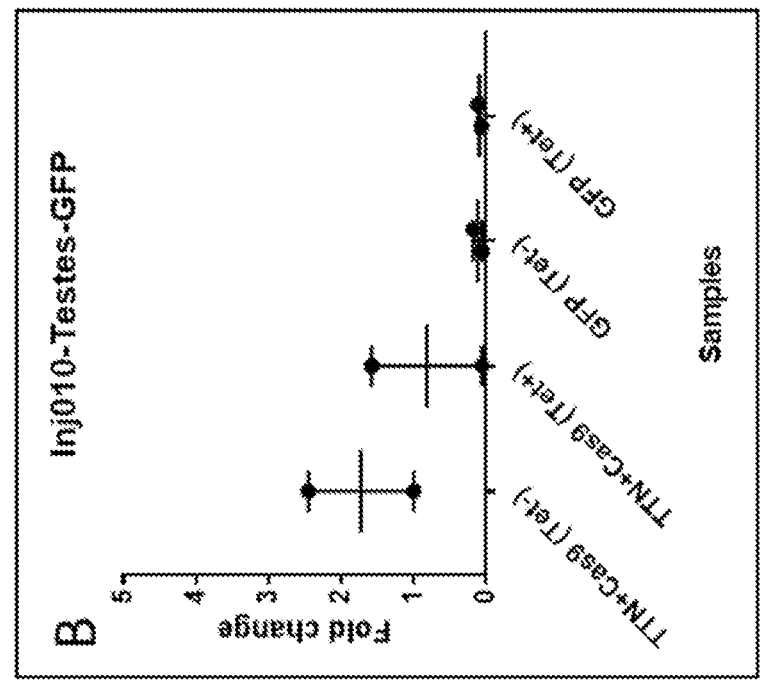
FIGS. 18A-18C demonstrate design and validation of a kill switch in vivo. A and B. GFP expression was detected in spleen and testes in mice injected with AAV-TTN-SAM-GFP and AAV-Cas9. C. qPCR was performed to detect virus copy numbers of in injected mice.
Figure 18B:
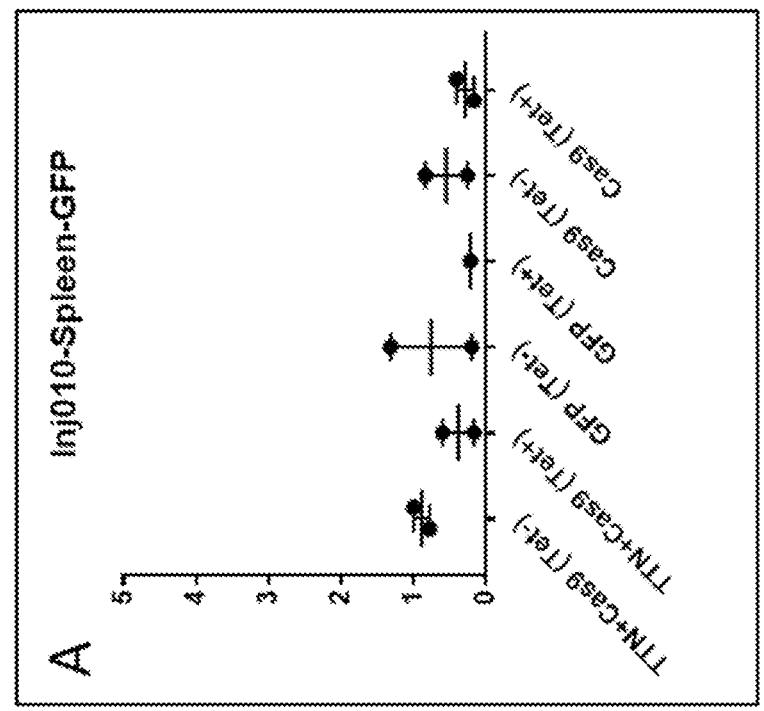
Figure 18C:
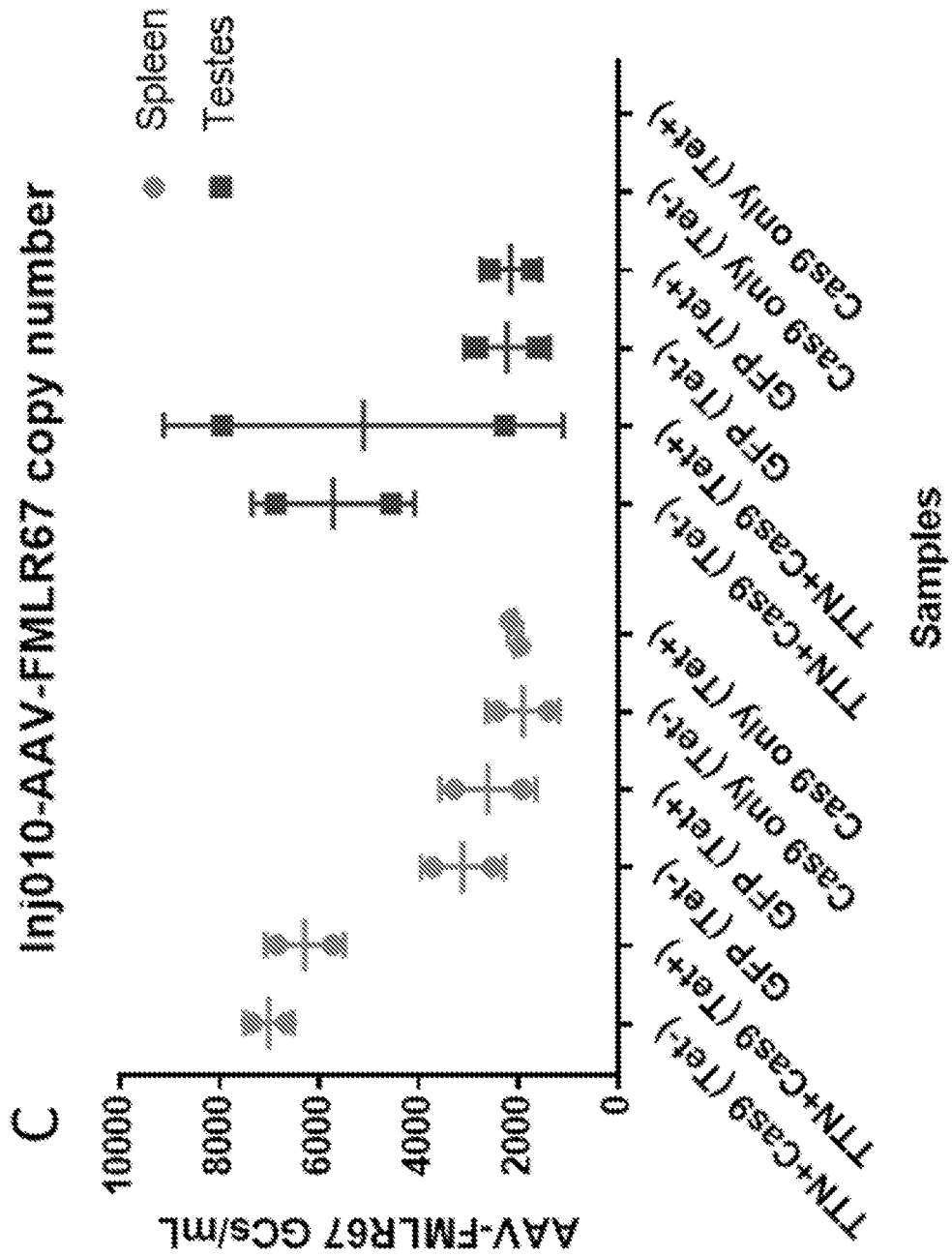

A baseline level of GFP expression was detected in spleen of all mice groups. GFP levels were higher in testes in mice groups injected with AAV-TTN-SAM-GFP and AAV-Cas9. See FIGS. 18A and 18B. qPCR was performed to detect copy numbers of virus injected. As shown in FIG. 18C, comparable viral copy numbers were detected between mice from each group.

Figure 19:
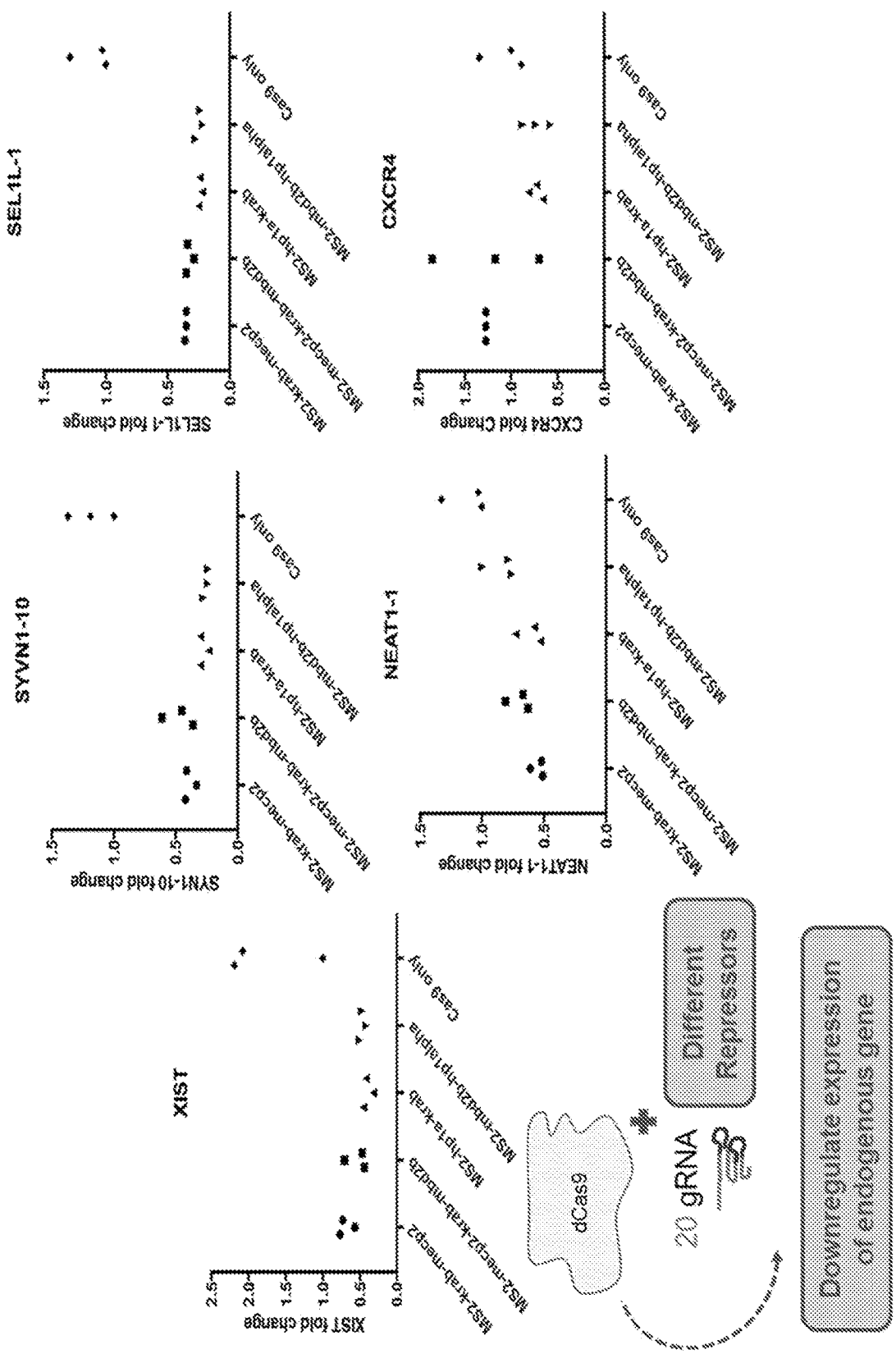
FIG. 19 demonstrates improved repression of endogenous gene using MS2-Hp1a-KRAB.

Next, we compared the repression level of several endogenous genes using different repressor proteins. The tested endogenous genes were XIST, SYVN1-10, SEL1L-1, NEAT1-1, and CXCR4. As shown in FIG. 19, increased repression of endogenous gene expression was obtained using MS2-Hp1a-KRAB. These data demonstrate that MS2-Hp1a-Krab is an efficient repressor for all the genes targeted.

Figure 20:
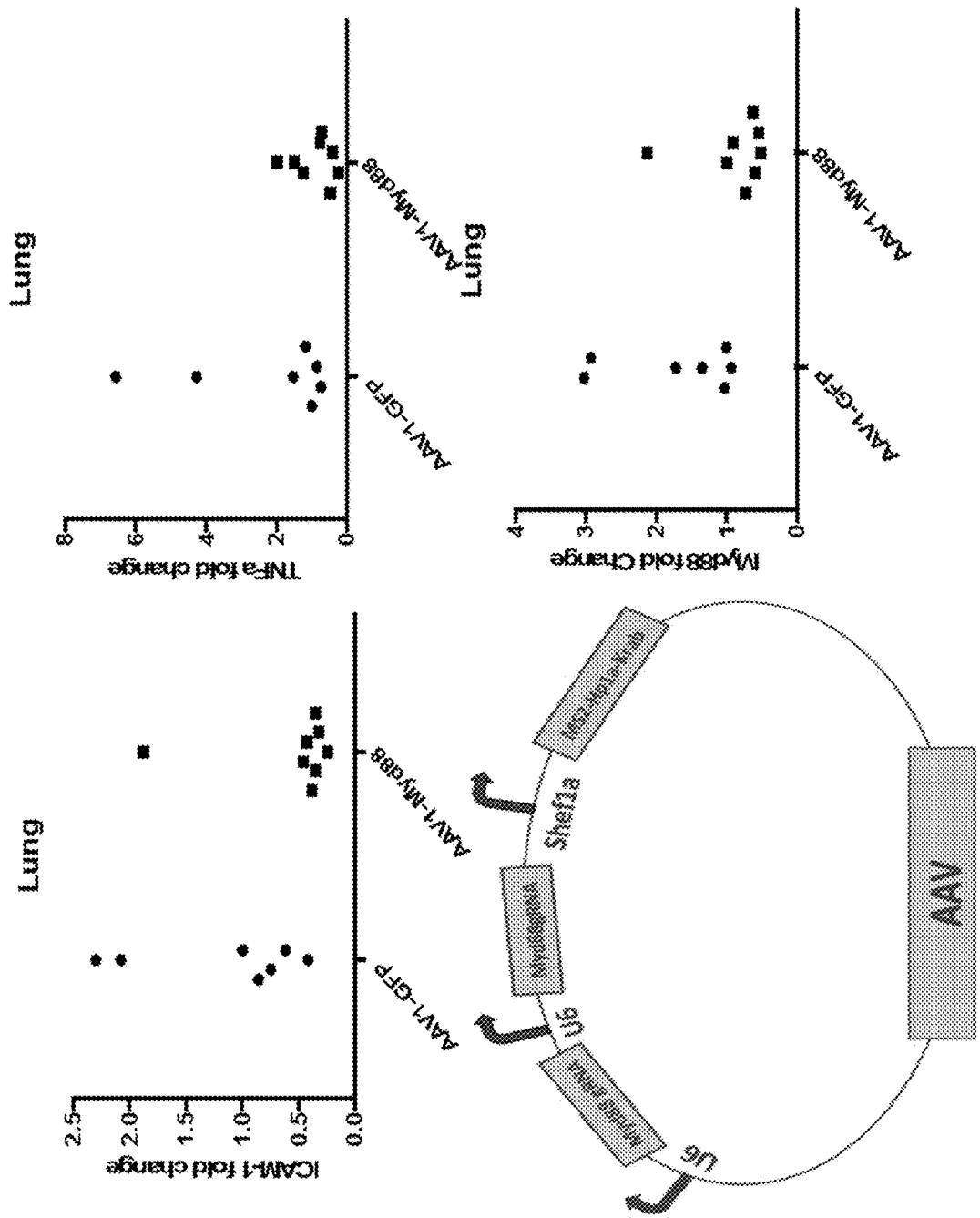
FIG. 20 demonstrates in vivo repression of Myd88 and inflammatory markers. AAV virus harboring a gRNA targeting Myd88 gene and a MS2hp1a repressor was injected to mice systemically. At 25 days post injection, the level of Myd88 expression and its downstream inflammatory markers in different tissues was assessed by qPCR FIG. 21 demonstrates in vivo repression of CXCR4 and inflammatory markers. AAV virus harboring a gRNA targeting CXCR4 gene and a MS2hp1a repressor was injected to mice systemically. At 25-days post injection, the level of CXCR4 expression and its downstream inflammatory markers in different tissues was assessed by qPCR.
Figure 21:
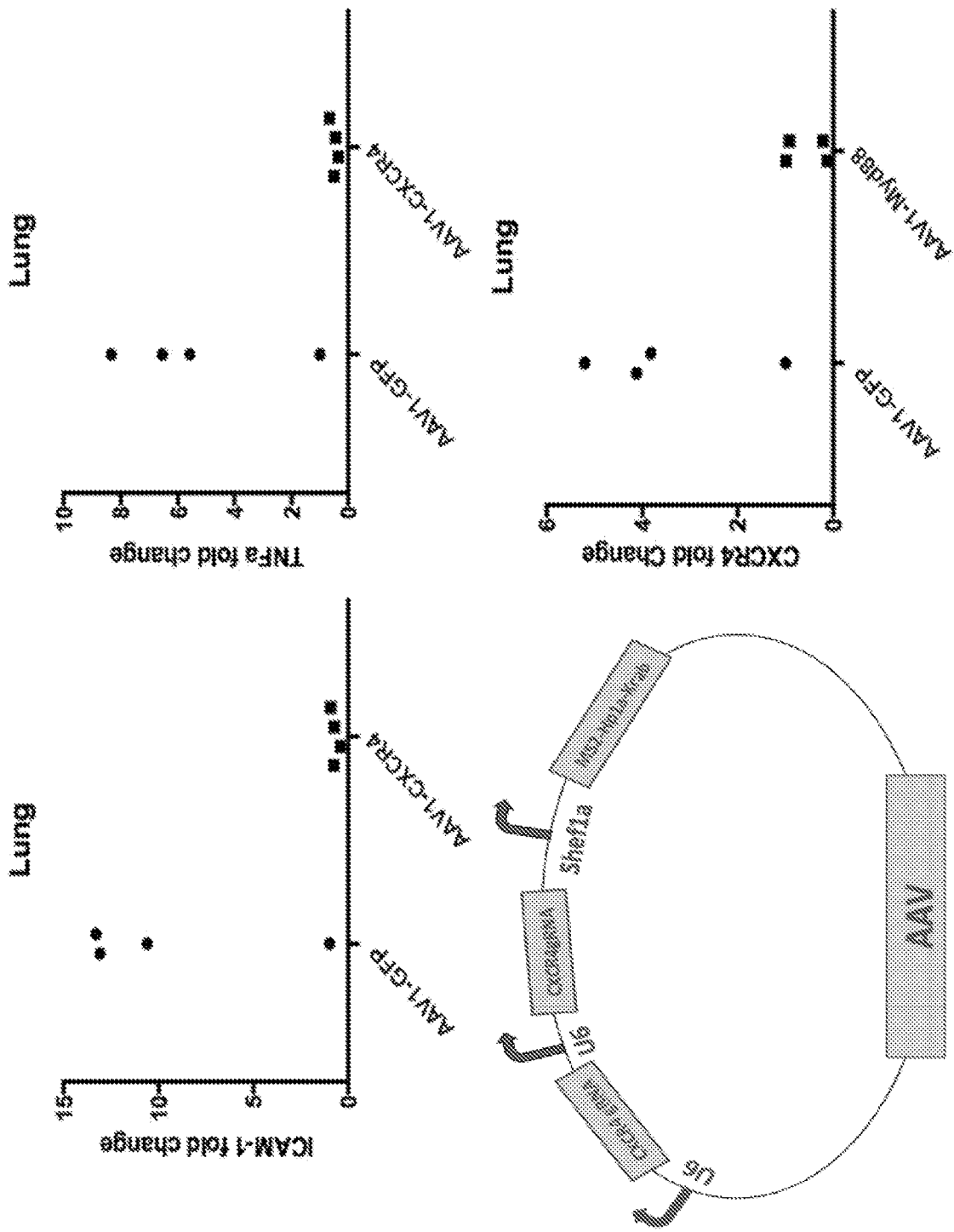

To test for in vivo repression, AAV virus harboring gRNAs targeting Myd88 and MS2hp1a repressor was injected to mice systemically. 25 days following injection, qPCR was performed to assay Myd88 expression levels and those of Myd88's downstream inflammatory markers (FIG. 20). These data demonstrate that mice that received CRISPR repressed the expression of Myd88, ICAM-1, and TNFα in lung. AAV virus harboring gRNA targeting CXCR4 gene and MS2hp1a repressor. As shown in FIG. 21, mice that received CRISPR repressed the expression of CXCR4, ICAM-1, and TNFα in lung.

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

We claim:

1. A synthetic regulatory system for modulating transcription in vivo, the system comprising a first and a second viral vector,
the first viral vector comprising:
(a) a nucleotide sequence encoding a multifunctional Cas nuclease operably linked to an inducible promoter;
(b) a nucleotide sequence encoding a first gRNA of 15 or less nucleotides (nt) in length that is complementary to at least a portion of a gene targeted for activation or repression;
the second viral vector comprising:
(c) a nucleotide sequence encoding a second gRNA of 16 nucleotides or greater in length that is complementary to at least a portion of the nucleotide sequence encoding (b), the second gRNA further comprising a regulatory control element configured to limit expression of the second gRNA, wherein the regulatory control element comprises a ligand-responsive ribozyme comprising a sensor component capable of detecting the presence of a small molecule signal or germ cell-specific signal and an actuator component configured for activation of the second gRNA whereby, in the presence of the small molecule signal or germ cell-specific signal, the second gRNA recruits the Cas nuclease for cleavage and disruption of the nucleotide sequence of (b);

(d) an activator of transcription of the nucleotide sequence encoding a multifunctional Cas nuclease or the nucleotide sequence encoding the first gRNA.

2. The system of claim 1, wherein the small molecule signal is selected from the group consisting of doxycycline, theophylline, tetracycline, thiamine pyrophosphate (TPP), S-adenosyl methionine (SAM), Flavin mononucleotide (FMN), P53, and NFκ-b.

3. The system of claim 1, wherein the first gRNA comprises a MS2 aptamer target site.

4. The system of claim 1, wherein the gene targeted for activation is a gene associated with tissue repair or wound healing.

5. The system of claim 1, wherein the Cas nuclease is Cas9.

6. The system of claim 1, wherein the Cas nuclease is fused to a functional domain selected from the group consisting of an activation domain, transcriptional activator, a transcriptional repressor, methyltransferase and a nuclease cleavage domain.

7. The system of claim 1, wherein the vectors are AAV delivery vectors.

8. A synthetic regulatory system for modulating a target gene in vivo comprising a first and a second viral vector,
the first viral vector comprising:
(a) a nucleotide sequence encoding a multifunctional Cas nuclease operably linked to a promoter;
(b) a nucleotide sequence encoding a first gRNA of 16 or greater nucleotides (nt) in length;
the second viral vector comprising:
(c) a nucleotide sequence encoding a second gRNA of 16 or greater nucleotides in length that is complementary to at least a portion of the nucleotide sequence encoding (b), comprising a ligand-responsive ribozyme comprising a sensor component and an actuator component configured for inducible activation of the second gRNA whereby, in the presence of a small molecule ligand, the second gRNA recruits the Cas nuclease for cleavage and disruption of the nucleotide sequence of (b);
(d) an activator of transcription of the nucleotide sequence encoding a multifunctional Cas nuclease or the nucleotide sequence encoding the first gRNA.

9. The system of claim 8, wherein expression of the first gRNA is driven by a CRISPR-repressible promoter (CRP) or a CRISPR-activatable promoter (CAP).

10. The system of claim 8, wherein the ligand-responsive ribozyme is induced by a small molecule selected from the group consisting of doxycycline, theophylline, tetracycline, thiamine pyrophosphate (TPP), S-adenosyl methionine (SAM), Flavin mononucleotide (FMN), P53, and NFκ-b.

11. The system of claim 8, wherein the vectors are AAV delivery vectors.

12. The system of claim 8, the Cas nuclease is Cas9 or Cas9-VPR.

13. A method of regulating a nucleic acid based therapeutic agent in vivo, the method comprising introducing the synthetic regulatory system of claim 1 into a cell having a nucleic acid based therapeutic agent, wherein the synthetic regulatory system modulates expression of the nucleic acid based therapeutic agent in the cell upon exposure to an inducer of the inducible promoter.

14. The method of claim 13, wherein the synthetic regulatory system is introduced into the cell using one or more DNA viruses.

* * * * *